US011859188B2

(12) United States Patent
Wu

(10) Patent No.: US 11,859,188 B2
(45) Date of Patent: Jan. 2, 2024

(54) DNA APTAMER, PHARMACEUTICAL COMPOSITION COMPRISING SAME, METHOD FOR INHIBITING CATALYTIC ABILITY OF TXNDC5, AND METHOD FOR PREVENTING OR TREATING ORGAN FIBROSIS

(71) Applicants: CHI-HUA FUNDATION, New Taipei (TW); Tiffany Wu, New Taipei (TW)

(72) Inventor: Wan-Lin Wu, Taipei (TW)

(73) Assignees: CHI-HUA FUNDATION, New Taipei (TW); Tiffany Wu, New Taipei (TW)

( * ) Notice: Subject to any disclaimer, the term of this patent is extended or adjusted under 35 U.S.C. 154(b) by 0 days.

(21) Appl. No.: 17/705,421

(22) Filed: Mar. 28, 2022

(65) Prior Publication Data

US 2023/0304019 A1 Sep. 28, 2023

(51) Int. Cl.
*C12N 15/115* (2010.01)
*A61P 9/00* (2006.01)
*A61P 9/04* (2006.01)

(52) U.S. Cl.
CPC .............. *C12N 15/115* (2013.01); *A61P 9/00* (2018.01); *A61P 9/04* (2018.01); *C12N 2310/16* (2013.01)

(58) Field of Classification Search
CPC ........................... C12N 15/115; C12N 2310/16
See application file for complete search history.

(56) References Cited

U.S. PATENT DOCUMENTS

2018/0095078 A1* 4/2018 Hong ................. G01N 33/5308

OTHER PUBLICATIONS

Wang et al. European Journal of Medical Research 27:145, pp. 1-10 (Year: 2022).*
Ying-Chun Shih et al., Endoplasmic Reticulum Protein TXNDC5 Augments Myocardial Fibrosis by Facilitating Extracellular Matrix Protein Folding and Redox-Sensitive Cardiac Fibroblast Activation, Circulation Research. Apr. 12, 2018; 122(8):1052-1068.
Tzu-Han Lee et al., Fibroblast-enriched endoplasmic reticulum protein TXNDC5 promotes pulmonary fibrosis by augmenting TGFB signaling through TGFBR1 stabilization, Nature Communications, (2020) 11:4254.
Yen-Ting Chen, et al., Endoplasmic reticulum protein TXNDC5 promotes renal fibrosis by enforcing TGF-β signaling in kidney fibroblasts, The Journal of Clinical Investigation, 2021; 131(5):e143645.
Chen-Ting Hung et al., Targeting ER protein TXNDC5 in hepatic stellate cell mitigates liver fibrosis by repressing hon-canonical TGFβ signalling, Gut Published Online, Dec. 21, 2021. , 10.1136/gutjnl-2021-325065.
Anthony M. Smith et al., A High-Throughput Turbidometric Assay for Screening Inhibitors of Protein Disulfide Isomerase Activity, Journal of Biomolecular Screening, 9, 614-620, doi:10.1177/1087057104265292 (2004).
Shih-Ming Tsao et al., Generation of Aptamers from A Primer-Free Randomized ssDNA Library Using Magnetic-Assisted Rapid Aptamer Selection, Scientific Reports, 7, 45478, doi:10.1038/srep45478 (2017).

* cited by examiner

*Primary Examiner* — Brian Whiteman

(57) ABSTRACT

A DNA aptamer, a pharmaceutical composition comprising the above DNA aptamer, a method for inhibiting the catalytic ability of TXNDC5 and a method for preventing or treating organ fibrosis are revealed. The DNA aptamer comprises a polynucleotide specifically binding to TXNDC5, the polynucleotide is selected from the group consisting of the nucleotide sequence of any one of SEQ ID NOS: 1-14. The pharmaceutical composition comprises the above DNA aptamers as an active ingredient. The method for inhibiting the catalytic ability of TXNDC5 comprises binding the above aptamers to TXNDC5. The method for preventing or treating organ fibrosis comprises administering an effective amount of the above aptamers to a subject.

12 Claims, 19 Drawing Sheets
(5 of 19 Drawing Sheet(s) Filed in Color)
Specification includes a Sequence Listing.

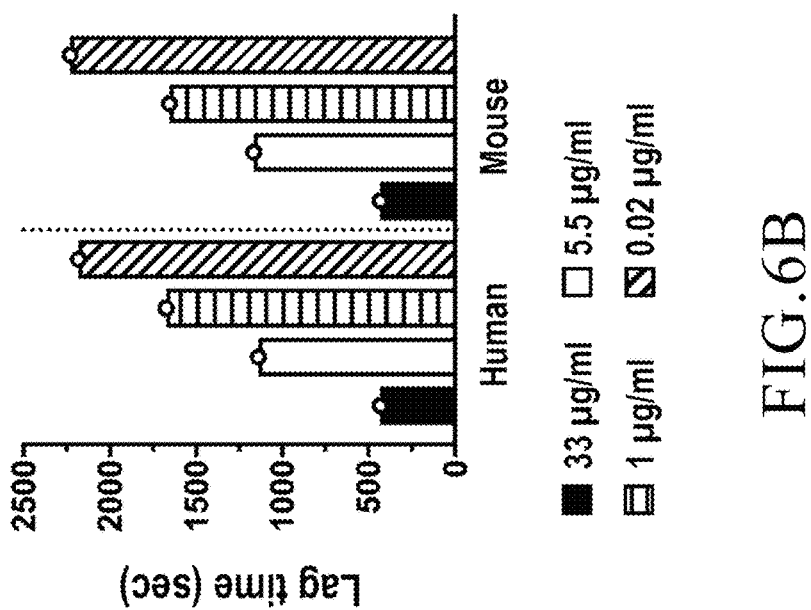
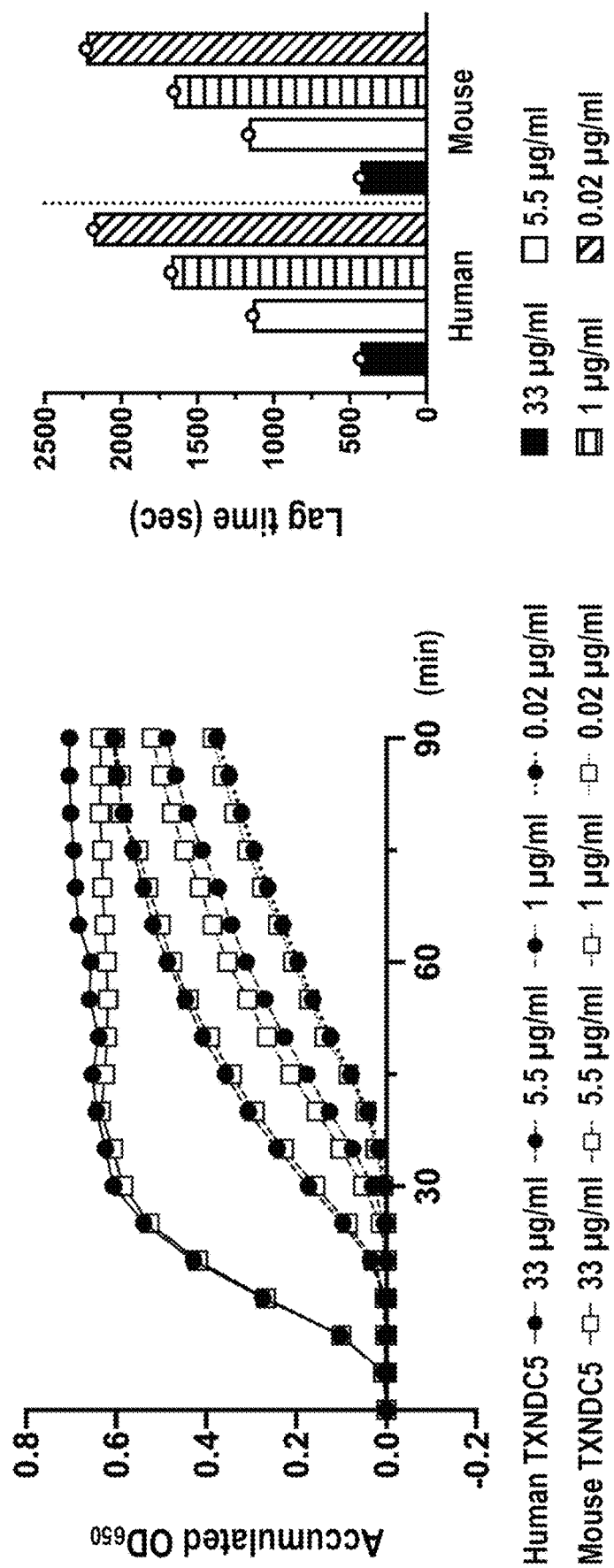
FIG.6B
FIG.6A

DNA APTAMER, PHARMACEUTICAL COMPOSITION COMPRISING SAME, METHOD FOR INHIBITING CATALYTIC ABILITY OF TXNDC5, AND METHOD FOR PREVENTING OR TREATING ORGAN FIBROSIS

REFERENCE TO A SEQUENCE LIST

This application refers to a "Sequence list" listed below, which is provided as an electronic document, created on Aug. 4, 2023, entitled "Sequence.txt" and being 5,115 bytes in size, the "Sequence list" is incorporated herein by reference in its entirety.

BACKGROUND OF THE INVENTION

1. Field of the Invention

The present disclosure relates to a DNA aptamer, a pharmaceutical composition comprising same, method for inhibiting catalytic ability of TXNDC5, 15 and method for preventing or treating organ fibrosis, more particularly, to a DNA aptamer capable of inhibiting catalytic ability of TXNDC5.

2. Description of the Related Art

Thioredoxin domain-containing 5 (TXNDC5) is an endoplasmic reticulum protein with the enzymatic activity of a protein disulfide isomerase in the endoplasmic reticulum. TXNDC5 facilitates the appropriate folding and the correct formation of disulfide bonds of cell proteins.

Recently, TXNDC5 is identified that it plays the functional role in the pathogenesis of many diseases. A study reports that TXNDC5 is a critical mediator of cardiac fibrosis and heart failure, TXNDC5 promotes cardiac fibrosis by facilitating extracellular matrix protein folding and induces cardiac fibrosis activation via redox-sensitive c-Jun N-terminal kinase signaling (Ying-Chun Shih et al. Endoplasmic Reticulum Protein TXNDC5 Augments Myocardial Fibrosis by Facilitating Extracellular Matrix Protein Folding and Redox-Sensitive Cardiac Fibroblast Activation. *Circ Res* 2018 Apr. 12; 122(8):1052-1068). The above study also reveals that loss of TXNDC5 protects against β agonist-induced cardiac fibrosis and contractile dysfunction.

TXNDC5 is also identified that it promotes pulmonary fibrogenesis by enhancing TGF1 signaling through facilitating the folding and stabilization of TGFBR1 in lung fibroblasts, and the inducing fibroblast-specific deletion of Txndc5 is able to mitigate the progression of BLM-induced PF and lung function deterioration (Tzu-Han Lee et al. Fibroblast-enriched endoplasmic reticulum protein TXNDC5 promotes pulmonary fibrosis by augmenting TGFβ signaling through TGFBR1 stabilization. *nature communications* 11:4254 (2020)).

It is demonstrated that TXNDC5 is a critical mediator of kidney fibrosis and targeted deletion of Txndc5 attenuates renal fibrogenesis in mouse models of chronic kidney disease (Y T Chen, P Y Jhao, C T Hung, Y F Wu, S J Lin, WC Chiang, SL Lin, KC Yang. Endoplasmic Reticulum Protein TXNDC5 Promotes Renal Fibrosis by Enforcing TGFβ Signaling in Kidney Fibroblasts. *Journal of Clinical Investigation* 2021 Mar. 1: 131(5): e143645).

In another study, it is revealed that TXNDC5 contributes to liver fibrosis by promoting hepatic stellate cells activity and extracellular matrix production through activating pro-fibrotic ERK and STAT3 signaling (CT Hung, TH Su, YT Chen, Y F Wu, Y T Chen, S J Lin, S L Lin, K C Yang. gutjnl. Gut 2021 Dec. 21: gutjnl-2021-325065).

BRIEF SUMMARY OF THE INVENTION

An objective of the present disclosure is to provide a DNA aptamer comprising a polynucleotide specifically binding to TXNDC5, wherein the polynucleotide is selected from the group consisting of the nucleotide sequence of any one of SEQ ID NOS: 1-14.

Regarding the DNA aptamer, the polynucleotide is the nucleotide sequence of SEQ ID NOS: 3.

Regarding the DNA aptamer, the polynucleotide is the nucleotide sequence of SEQ ID NOS: 7.

Regarding the DNA aptamer, the polynucleotide is the nucleotide sequence of SEQ ID NOS: 11.

To achieve at least the above objective, the present disclosure provides a pharmaceutical composition comprising the above DNA aptamers as an active ingredient.

Regarding the pharmaceutical composition, the DNA aptamer is a therapeutic agent against cardiac fibrosis.

Regarding the pharmaceutical composition, the DNA aptamer is a therapeutic agent against heart failure.

Regarding the pharmaceutical composition, the DNA aptamer is a therapeutic agent against liver fibrosis.

Regarding the pharmaceutical composition, the DNA aptamer is a therapeutic agent against renal fibrosis.

Regarding the pharmaceutical composition, the DNA aptamer is a therapeutic agent against chronic kidney diseases.

Regarding the pharmaceutical composition, the DNA aptamer is a therapeutic agent against pulmonary fibrosis.

To achieve at least the above objective, the present disclosure further provides a method for inhibiting the catalytic ability of TXNDC5, comprising binding the above aptamers to TXNDC5.

To achieve at least the above objective, the present disclosure further provides a method for preventing or treating organ fibrosis, comprising administering an effective amount of the above aptamers to a subject in need thereof.

Regarding the method, the organ fibrosis is cardiac fibrosis.

Regarding the method, the organ fibrosis is liver fibrosis.

Regarding the method, the organ fibrosis is renal fibrosis.

Regarding the method, the organ fibrosis is pulmonary fibrosis.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 6A shows a graph of Optimized concentrations of Human TXNDC5 and mouse TXNDC5.

FIG. 6B shows a graph of lag time of entire TXNDC5 protein.

DETAILED DESCRIPTION OF THE INVENTION

Figure 1:
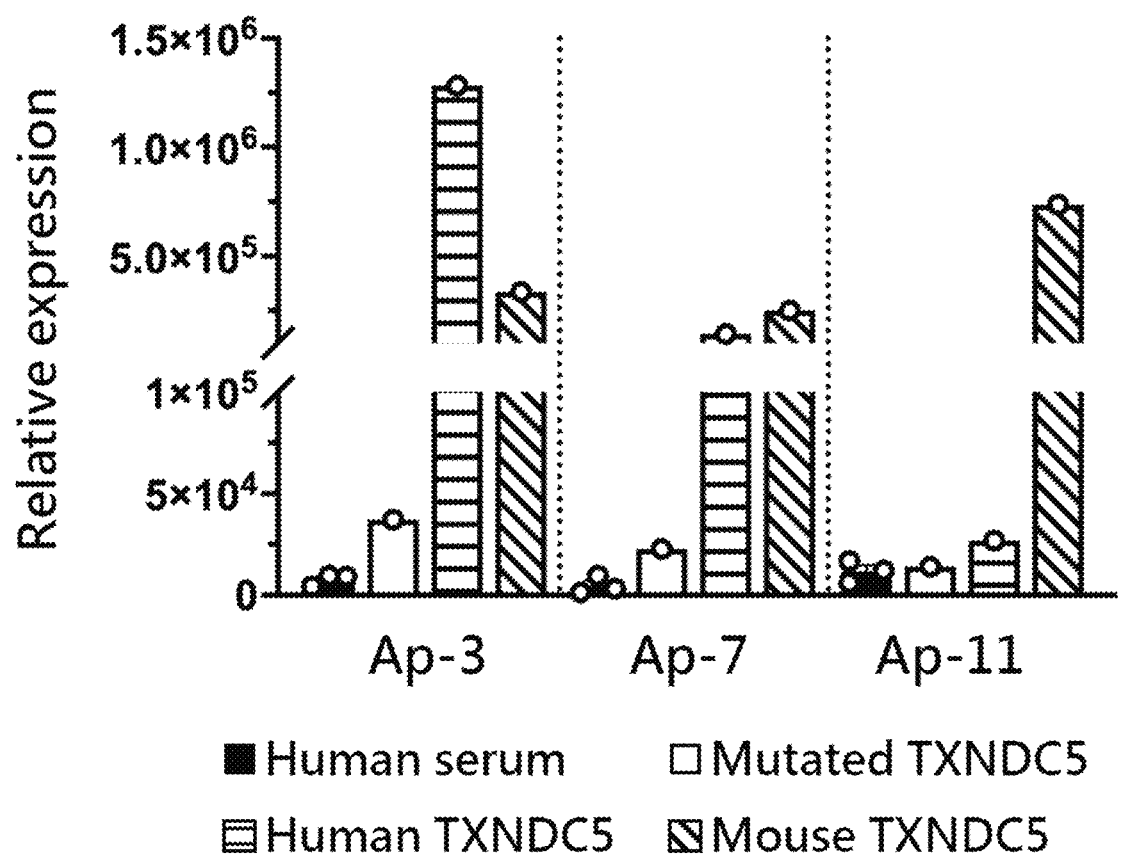
FIG. 1 shows a graph illustrating the binding affinity of aptamers to TXNDC5.
Figures 2A, 2B:
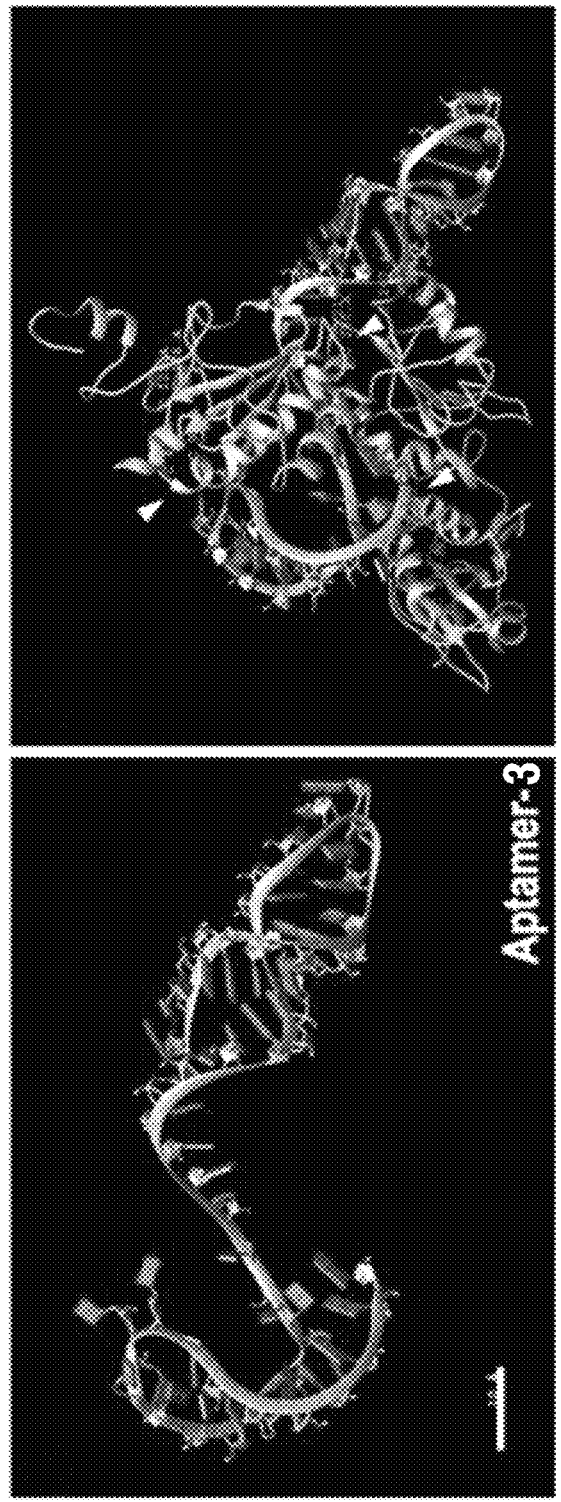
FIG. 2A shows a picture of a 3D structure of Apt-3.
FIG. 2B shows a picture of docking simulation of Apt-3 and wild-type human TXNDC5. Arrowheads: CGHC catalytic motif.
Figures 3A, 3B:
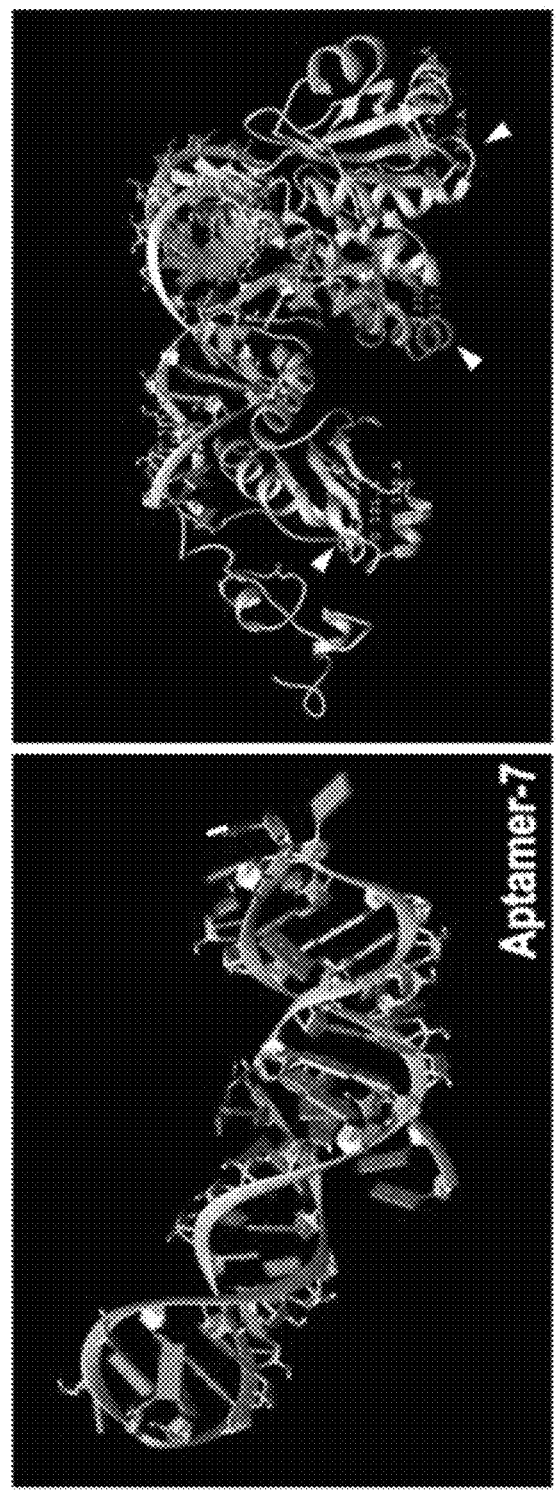
FIG. 3A shows a picture of a 3D structure of Apt-7.
FIG. 3B shows a picture of docking simulation of Apt-7 and wild-type human TXNDC5. Arrowheads: CGHC catalytic motif.
Figures 4A, 4B:
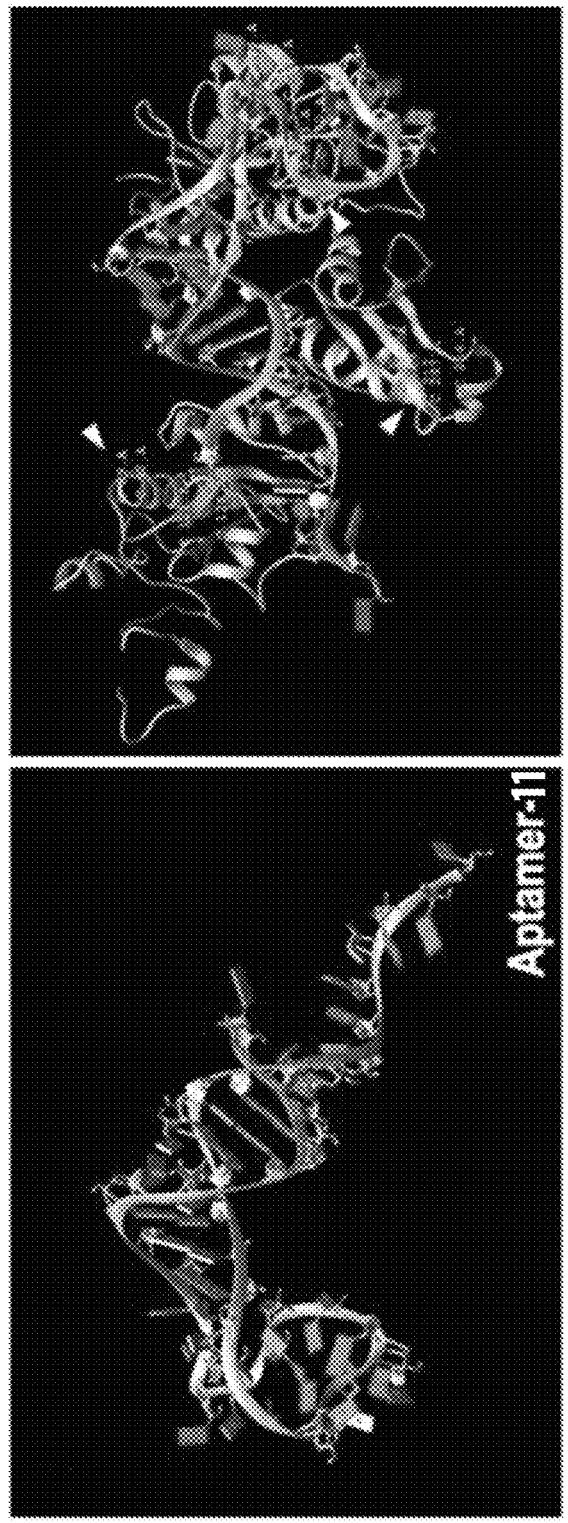
FIG. 4A shows a picture of a 3D structure of Apt-11.
FIG. 4B shows a picture of docking simulation of Apt-11 and wild-type human TXNDC5. Arrowheads: CGHC catalytic motif.

To facilitate understanding of the object, characteristics and effects of this present disclosure, embodiments together with the attached drawings for the detailed description of the present disclosure are provided.

Magnetic-Assisted Rapid Aptamer Selection (MARAS)

According to the previous studies, targeting TXNDC5 could be a novel therapeutic approach against multiple fibrosis-related diseases, such as cardiac fibrosis, heart failure, liver fibrosis, renal fibrosis, chronic kidney diseases and pulmonary fibrosis.

A strategy of targeting TXNDC5 is providing DNA aptamer(s) capable of binding TXNDC5 with high specificity and affinity and inhibiting the catalytic ability of TXNDC5. To this end, magnetic-assisted rapid aptamer selection, a novel magnetic-based aptamer screening method, is used to identify multiple TXNDC5-targeting aptamers.

The method of selecting TXNDC5-targeting aptamers via MARAS is set forth as following.

First, wild-type TXNDC5, catalytic-death TXDNC5 and human serum are biotinylated by EZ-Link NHS-SS-Biotin Kit (Thermo Scientific) according to the manufactures' instructions. A total 100 μs of each biotinylated protein (including the above biotinylated wild-type TXNDC5, catalytic-death TXDNC5 and human serum) is mixed with 50 μl of streptavidin-coated magnetic beads (SA-MNPs) at 4° C. overnight.

The mixture of each biotinylated protein and the magnetic beads (MNPs) correspondingly reacting with the biotinylated protein is then subjected to magnetic separation by magnetic stand to remove the unbound biotinylated proteins. The proteins conjugated MNPs (TXNDC5-MNPs) are washed with the binding buffer (the binding buffer contains 20 mM Tris-Cl (pH 7.6), 150 mM NaCl, 50 mM KCl, 2 mM $MgCl_2$, 1 mM $CaCl_2$) and 0.05% Tween-20, the following terms "binding buffer" refers to the binding buffer containing the same components described herein) and stored in the same binding buffer at 4° C. or processed for following experiments.

Further, random 50 nucleotides of ssDNA library (aptamers library) are chemically synthesized in 250 nM scale at Integrated DNA Technologies (MedClub Scientific, Taiwan) as starting library. Each aptamer (ssDNA) is composed of the central 20 randomized oligonucleotides, which are flanked with two fixed stem-loop sequences at both ends (5'-AGCAGCACAGAGGTC-N20-GCGTGCTACCGT-GAA-3') for PCR amplification and sequencing (Tsao, S. M et al. Generation of Aptamers from A Primer-Free Randomized ssDNA Library Using Magnetic-Assisted Rapid Aptamer Selection. Sci Rep 7, 45478, doi:10.1038/srep45478 (2017)). Two set of primers: 5'-AGCAGCACAGAGGTC-3' (SEQ ID NO: 15) and 5'-TT-CACGGTAGCACGC-3' (SEQ ID NO: 16) are utilized.

After the above ssDNA library has been established, 0.5 μl of randomized oligonucleotide solution (the initial concentration: 100 μM) is used as the starting library and diluted to 10 μl by adding 9.5 μl of the binding buffer (the final concentration of the randomized oligonucleotide solution is 5 The above solution is heated to 95° C. for 5 min and then quickly snapped to 4° C. to make ssDNA form secondary structures. After ssDNA in the above solution has formed into secondary structures, the above solution is stayed at room temperature for 30 min. The first positive selection round is performed by incubating TXNDC5-MNPs (mouse wild type TXNDC5) and the folding oligonucleotide (ssDNA) in the binding buffer for 30 min at room temperature, thereby TXNDC5-MNPs and the folding oligonucleotide are bound together to form aptamer-TXNDC5-MNPs complexes. The aptamer-TXNDC5-MNPs complexes are placed inside the MARAS platform and subjected to a rotating magnetic field with 40-50 KHz and strength of 14 gauss for 10 min. After the above treatment of the rotating magnetic field, the aptamer-TXNDC5-MNPs complexes are stirred by pipetting every 2.5 min to avoid agglomeration. The aptamer-TXNDC5-MNPs complexes are retained and washed three times with 200 μl of the binding buffer. The aptamer-TXNDC5-MNPs complexes are re-suspended into 100 μl of the binding buffer and processed for next positive selection round (human wild type TXNDC5) in identical procedures for refining the aptamers that are attracted by both species of TXNDC5 (human and mouse).

Subsequently, for negative selection, a library (ssDNA) from the previous 2 round positive selections is incubated with negative serum-MNPs at room temperature for 30 min. After magnetic separation, aptamers bound with negative serum-MNPs are removed. The collected supernatants are continuously processed to other negative-MNPs (2 rounds of serum-MNPs and 1 round of catalytic-death TXNDC5-MNPs) as the aforementioned negative-selection procedures. The final supernatant containing the aptamer-TXNDC5-MNPs complexes which are not capable of binding to serum and enzymatic-death TXNDC5 is collected.

The target-bound aptamers are amplified by PCR and the amplicons of the target-bound aptamers are purified by PCR purification Kit (MinElute PCR purification kit (QIAGEN)) following the manufacturer's instructions. The purified amplicons of the target-bound aptamers are then subcloned into a pGEM-T Easy vector and transformed into DH5a competent cells. The randomly chosen colonies are purified using a High-Speed Plasmid Mini Kit (Geneaid, Taipei, Taiwan) and subjected to sequencing (Genomics, Taiwan). The detail sequences of 14 TXNDC5-bound aptamers are listed in Table 1.

TABLE 1

List of TXNDC5-hit aptamers

| Number | Sequences |
|---|---|
| Aptamer-1 (SEQ ID NO: 1) | AGC AGC ACA GAG GTC TAG ATG TAA AGG TAC CTC AGG CGT GCT ACC GTG AA |
| Aptamer-2 (SEQ ID NO: 2) | AGC AGC ACA GAG GTC CCT TTA AGG CTT TTG GTC CGG CGT GCT ACC GTG AA |
| Aptamer-3 (SEQ ID NO: 3) | AGC AGC ACA GAG GTC AAT GTA ATC TTT ATC TAT CGG CGT GCT ACC GTG AA |
| Aptamer-4 (SEQ ID NO: 4) | AGC AGC ACA GAG GTC TCG TTT TAC TCT CGT GTT TGG CGT GCT ACC GTG AA |
| Aptamer-5 (SEQ ID NO: 5) | AGC AGC ACA GAG GTC ATC ATC TGG ACT CGG AAT CGG CGT GCT ACC GTG AA |
| Aptamer-6 (SEQ ID NO: 6) | AGC AGC ACA GAG GTC GGT GTA TGA CTT TAT TTC CGG CGT GCT ACC GTG AA |
| Aptamer-7 (SEQ ID NO: 7) | AGC AGC ACA GAG GTC AGG AAC CTT ATG CCT ATG TAG CGT GCT ACC GTG AA |
| Aptamer-8 (SEQ ID NO: 8) | AGC AGC ACA GAG GTC CCT ATC AAC CAC ACC ATC TTG CGT GCT ACC GTG AA |
| Aptamer-9 (SEQ ID NO: 9) | AGC AGC ACA GAG GTC TAT TGT GAA CTT TTT CAG CGG CGT GCT ACC GTG AA |
| Aptamer-10 (SEQ ID NO: 10) | AGC AGC ACA GAG GTC CCT CTC CGG TAT GCT TAT TTG CGT GCT ACC GTG AA |
| Aptamer-11 (SEQ ID NO: 11) | AGC AGC ACA GAG GTC TCT TAT TAC TCT CCC GTA CCG CGT GCT ACC GTG AA |
| Aptamer-12 (SEQ ID NO: 12) | AGC AGC ACA GAG GTC GAC TCT TGA TTT CCT TGC ATG CGT GCT ACC GTG AA |

TABLE 1-continued

List of TXNDC5-hit aptamers

| Number | Sequences |
|---|---|
| Aptamer-13 (SEQ ID NO: 13) | AGC AGC ACA GAG GTC GAC TCT TGA TTT CCT TGC ATG CGT GCT ACC GTG AA |
| Aptamer-14 (SEQ ID NO: 14) | AGC AGC ACA GAG GTC ATT CGA TTG TTT TAC AAT TTG CGT GCT ACC GTG AA |

For further investigating the inhibitory effects of aptamers on TXNDC5 catalytic function, aptamer-3 (Ap-3), aptamer-7 (Ap-7) and aptamer-11 (Ap-11) are representatively selected in the following experiments.

Reverse Validation of Isolated Aptamers

The 100 nM of aptamer-3, aptamer-7 and aptamer-11 are folded in the binding buffer via the procedures as mentioned above. 20 nM of Aptamer-3, aptamer-7 and aptamer-11 are taken individually and hybridized with positive-(mouse and human TXNDC5, 5 µl) and negative-(serum and catalytic-death TXNDC5, 5 µl) MNPs, and the hybridized aptamers-MNPs are processed according to the above MARAS procedures. Aptamer-3, aptamer-7 and aptamer-11 bound with MNPs are collected and eluted by heating to 95° C. for 5 min in 100 µl ddH$_2$O.

The amounts of aptamer-3, aptamer-7 and aptamer-11 are detected by q-PCR and the relative expression levels are utilized as outcomes. The process of detecting the amounts of aptamer-3, aptamer-7 and aptamer-11 by q-PCR is set forth as following. To measure the relative expression of aptamer-3, aptamer-7 and aptamer-11, the q-PCR is performed in 96-well plates with BioRad CFX Connect system. The fivefold-diluted eluted aptamer-3, aptamer-7 and aptamer-11 are individually dissolved in test tubes filled with 100 µl of RNase-free water. The relative expression of aptamer-3, aptamer-7 and aptamer-11 is performed by q-PCR in 96-well plates using BioRad CFX Connect system. A volume of 10 µl q-PCR mixture in the presence of 5 µl 2x_SYBR Green PCR master mix (BioRad), 1 µl of forward aptamer primer (1 Integrated DNA Technologies, IDT), 1 µl of reverse aptamer primer (1 Integrated DNA Technologies, IDT) and 3 µl of eluted aptamers is utilized for q-PCR reaction. The parameters for q-PCR are 95° C. for 3 min; 40 cycles at 94° C. for 30 sec, 60° C. for 30 sec, and 72° C. for 30 sec.

As show in FIG. 1, aptamer-3, aptamer-7 and aptamer-11 having strong binding with the positive controls and neglectable binding for negative controls are observed. Aptamer-3 reveals the specific binding affinity toward the human-TXNDC5 and the mouse-TXNDC5. Aptamer-11 reveals the specific and strong binding affinity toward the mouse-TXNDC5.

Aptamer Structure and Aptamer/TXNDC5 Docking Site Prediction

To determine if the TXNDC5-targeting aptamers identified above interact with the catalytic domains of TXNDC5, the 3D structure of aptamer-3, aptamer-7 and aptamer-11 and plausible protein docking sites were predicted using computational modeling. Aptamer structure and aptamer/TXNDC5 docking site prediction is performed in the following procedures.

First, the secondary structures of aptamer-3, aptamer-7 and aptamer-11 are predicted by M-fold DNA folding web software (unafold.rna.albany.edu), based on free energy minimization techniques. For setting the parameters of M-fold DNA folding form, the initial sequences of aptamer-3, aptamer-7 and aptamer-11 are set as a linear at a temperature of 25° C. and ionic concentration of 150 mM Na$^+$, 2 mM of Mg$^{2+}$. The computing is executed in the case that only fold configurations within 5% from the minimum free energy, and it is considered that a maximum number of folds is no limited to the maximum distance between paired bases. Next, the isolated ssDNA aptamer-3, aptamer-7 and aptamer-1 are modified as RNA aptamers and predicted via RNAComposer (rnacomposer.cs.put.poznan.pl) based on the secondary structures. Finally, the docking sites of individual aptamer and structure of wild type human TXNDC5 (I-TASSER, zhanglab.ccmb.med.umich.edu) are predicted through the PatchDock server (bioinfo3d.cs.tau.ac.il). The protein data bank (PDB) code for both aptamer (ligand molecule) and TXNDC5 (receptor molecule) is selected and evaluated at low valve of root mean square deviation (RMSD, 4 Å) with enzyme-inhibitor type.

The results of prediction are shown in FIGS. 2A, 2B, 3A, 3B, 4A, 4B, it is observed that all three individual aptamers exhibit single (Ap-11) or double stem-loop at its 3' and 5' ends (Ap-3 and -7) structures with free energy values (Ap-3, $\Delta G$=−4.29 kcal/mol, Ap-7, −2.66 kcal/mol, Ap-11, −7.20 kcal/mol). The result of predictions of 3D structures and docking sites demonstrate that aptamer-3, aptamer-7 and aptamer-11 anchor robustly on the wild type human TXNDC5 (FIG. 2 A-4B), and the binding positions for aptamer-3, aptamer-7 and aptamer-11 may dock approximately to the catalytic thioredoxin (CGHC) domains, it further reveals the potential of TXNDC5-targeting aptamers as potent antagonists against the disulfide isomerase activity of TXNDC5.

Dissociation Constant ($K_d$) of Aptamer-3 and Aptamer-7

For further determining the binding efficiency of TXNDC5-targeting aptamers, the $K_d$ values, as the indicator of aptamer and target molecule interaction, of aptamer-3 and aptamer-7 are measured by q-PCR, and the results were fitted with nonlinear regression. The method of measuring the $K_d$ values of aptamer-3 and aptamer-7 is illustrated as following.

Aptamer-3 and aptamer-7 are isolated and progressively diluted in series from 100 to 3.125 nM, aptamer-3 and aptamer-7 are folded in the binding buffer as the procedures mentioned above. Equal amounts of either mouse-MNPs or humane-MNPs are mixed with aptamer-3 and aptamer-7 and followed the MARAS and q-PCR procedure as described above to specifically bind to aptamer-3 and aptamer-7. The $K_d$ values of aptamer-3 and aptamer-7 are measured by fitting the results of each Ct value from q-PCR and the concentrations in a nonlinear regression through PRISM 8 (Graphpad). Each result is performed in duplicate to reduce the errors.

Figures 5A, 5B:
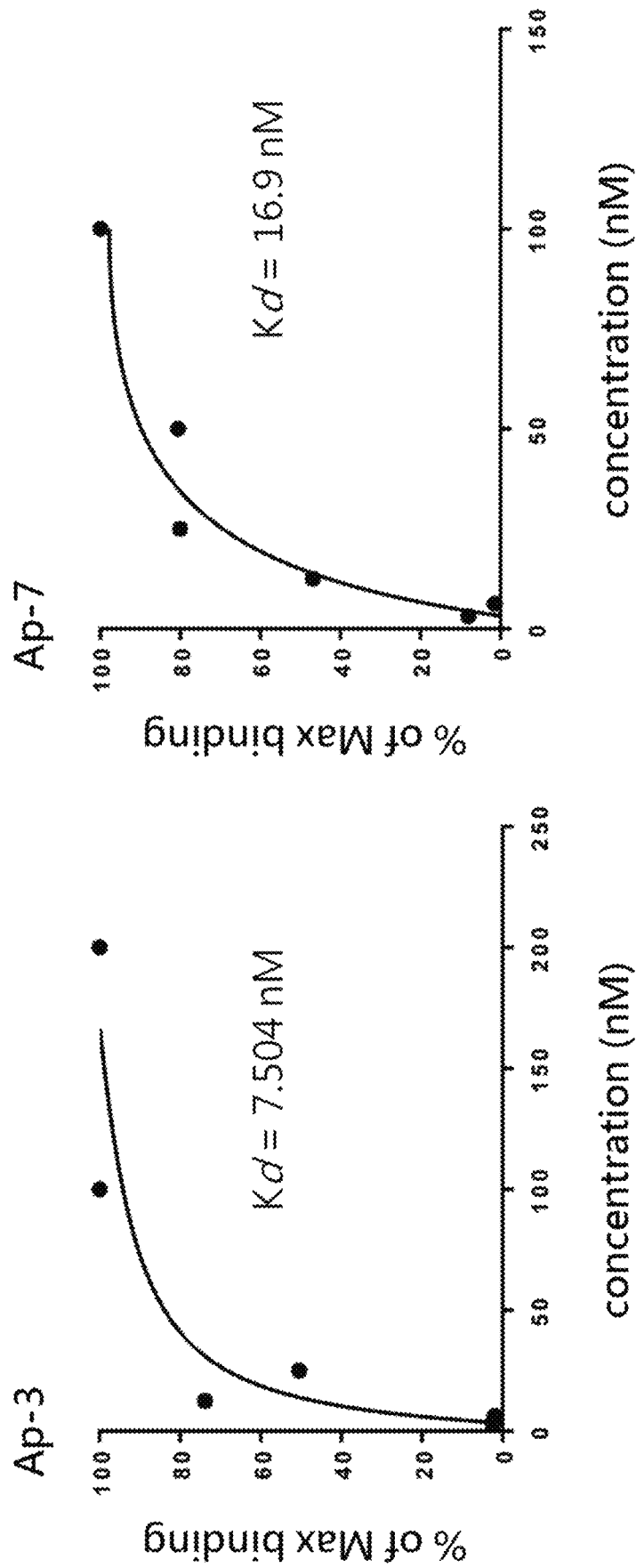
FIG. 5A shows a graph revealing dissociation constants of Apt-3.
FIG. 5B shows a graph revealing dissociation constants of Apt-7.

As shown in FIGS. 5A and 5B, the $K_d$ value of Ap-3 for mouse TXNDC5 is 7.504 nM and the $K_d$ value of Ap-7 for human TXNDC5 is 16.9 nM, it is demonstrated that the TXNDC5-targeting aptamers are capable of binding with TXNDC5 protein sensitively.

Insulin Reduction Assay

For determining the potency of individual aptamer on inhibiting the disulfide isomerase activity of TXNDC5, an insulin turbidimetric assay is performed.

For performing the insulin turbidimetric assay, two isolated thioredoxin domains of TXNDC5 (Trx1 and Trx2) and TXNDC5 protein are prepared as following.

TXNDC5 individual domains, Trx1 and Trx2, which have relative highest catalytic functions, are synthesized at the Yao-Hong Biotechnology Inc (Taiwan) with a purity grade of >85% validating through high performance liquid chromatography (HPLC). The purified Trx1 and Trx2 peptides which represent in the powder form are resuspended in 1:3 Acetonitrile/H$_2$O mixture at 1 mg/ml concentration. TXNDC5 Trx1 sequences: skhlytadm fthgiqsaah fvmffapwcg hcqrlqptwn dlgkynsme dakvyvakvd ctahsdvcsa qgvrgyptlk lfkpgqeavk yqgprdfqtl enwmlqtlne (SEQ ID NO: 17); TXNDC5 Trx2 sequences: g lyelsanfe lhvaqgdhfi kffapwcghc kalaptweql alglehsetv kigkvdctqh yelcsgnqvr gyptllwfrd gkkvdqykgk rdleslreyv esqlqrte (SEQ ID NO: 18).

High purity of wild type human-TXNDC5, mouse-TXNDC5 and catalytic mutated human-TXNDC5 are generated through baculovirus expression vector system at Sino Biological (Biotools, Taiwan). First, the flanking selected restriction fragments of TXNDC5 cDNA are added by PCR (provided by Sino Biological Inc), then shuttled to the baculovirus vector, the baculovirus vector containing TXNDC5 cDNA are transfected into multiple insect cells for encoding desired entire TXNDC5 protein. Various recombinant TXNDC5 proteins are purified from the soluble fractions of the cell lysates using Ni-purification column. The fractions containing desired entire TXNDC5 are enriched and further dissolved in the formulation buffer (20 mM PBS, 300 mM NaCl, 10% glycerol, pH 7.5). Purified TXNDC5 proteins are aliquoted and stored at −80° C. or processed for assays.

Before performing the insulin reduction tubidometric assay for measuring the effects of aptamer titration toward TXNDC5, the optimization of the reductase concentrations of TXNDC5 Trx1 and Trx2 or entire TXNDC5 protein for insulin turbidimetric assay is established according to the method of Smith, A. M. et al. (Smith, A. M. et al. A high-throughput turbidometric assay for screening inhibitors of protein disulfide isomerase activity. J. Biomol. Screen. 9, 614-620, doi:10.1177/1087057104265292 (2004)) to achieve a significant signal-to-noise ratio (SNR). The assays are carried out in 384-well plate (Greiner) and a volume of 30 μl of the solution in the presence of final concentrations of 0.16 mM insulin (Sigma-Aldrich) and the reductase. Entire TXNDC5 protein (human or mouse) (33, 1 and 0.02 μg/ml, FIG. 6A) or TXNDC5 peptide (Trx1 or Trx2) (5.6, 2.8, 1.12 and 0.28 FIG. 6C) varies concentrations in an assay buffer (100 mM potassium phosphate and 0.2 mM EDTA, pH 7.0). The 5 μl of 3.5 mM DTT in the final concentration 0.5 mM is added to initiate the reaction, and the reaction is monitored at 650 nm on a Synergy HTX Multi-mode reader (BioTek) for 90 mins at 37° C. The accumulated OD$_{650nm}$ and lag time are presented for validating the optimized concentration of reductases. When a 3-fold to 6-fold SNR is obtained, the indicated concentration of the reductases is decided for subsequent insulin reduction tubidometric assays.

Figure 6D:
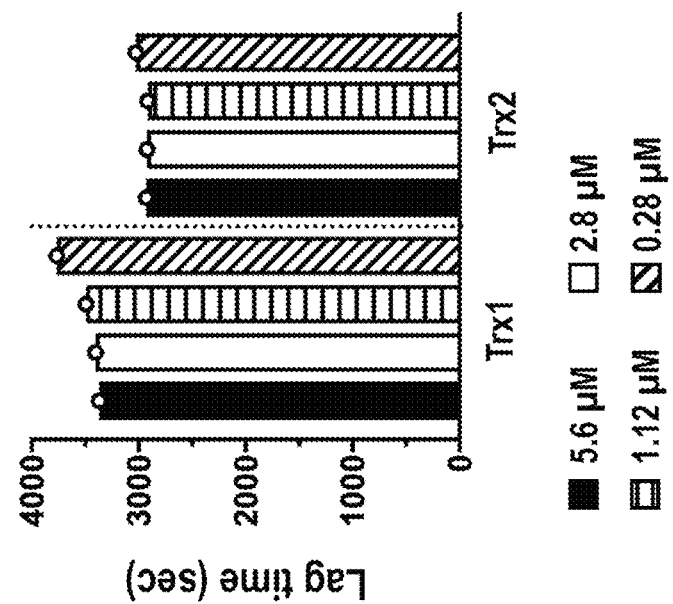
FIG. 6D shows a graph of lag time of Trx domain.
Figure 6C:
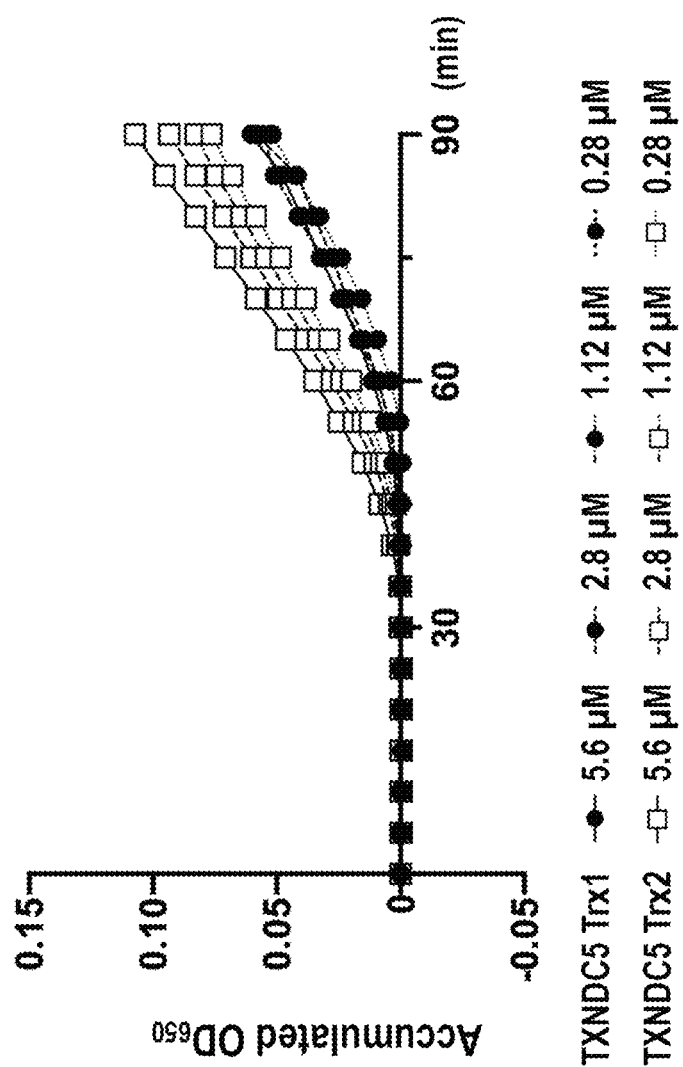
FIG. 6C shows a graph of Optimized concentrations of Trx domain.

The results of the optimization of the reductase concentrations of TXNDC5 Trx1 and Trx2 or entire TXNDC5 protein for insulin turbidimetric assay are shown in FIGS. 6A-6D, highest dose of TXNDC5 (33 μg/ml) exhibits about 5%, 20% and 40% increase in the end-point turbidities comparing to 5.5 μg/ml, 1 μg/ml and 0.02 μg/ml of TXNDC5, respectively (FIG. 6A). The isomerase reduction reactions were accelerated in a dose-dependent manner as the dramatic turbidity, the isomerase reduction reactions were obtained within 10 mins after addition of dithiothreitol (DTT) at highest amount of TXNDC5. The onset times of chemical reduction of insulin are markedly delayed approximately up to 2250 secs with diluted dose of TXNDC5 (FIG. 6B), and the onset times of chemical reduction of insulin are markedly delayed approximately up to 3700 secs with diluted dose of Trx1 and Trx2 (FIG. 6D). For individual Trx domains of TXNDC5, Trx1 and Trx2, both domains display relative longer reaction time and weaker kinetic reactions when they compare with full-length TXNDC5 protein (FIG. 6A-6D), as entire TXNDC5 protein could catalyze reductive reaction faster (thereby with shorter onset time) in a dose-dependent manner (FIGS. 6B and 6D).

To validate that the formation of precipitated insulin chains were resulted from catalytic functions of TXNDC5, TXNDC5 Trx1 and Trx2 or entire TXNDC5 protein reacts with hydrogen peroxide ($H_2O_2$) or protein disulfide isomerase inhibitor 16F16 (50 μm), separately. The reductase activities of TXNDC5 Trx1 and Trx2 and entire TXNDC5 protein are assayed by insulin reduction assay. The assays are carried out in 384-well plate (Greiner), and a volume of 30 μl of the solution in the presence of final concentrations of 0.16 mM insulin (Sigma-Aldrich) and the reductase is prepared. 5.6 μM TXNDC5 peptides (Trx1 and Trx 2, FIG. 7A), μg/ml entire TXNDC5 protein (FIG. 7B) or 10 μs protein from each cell lysates (human hepatic stellate cell LX2 with wild-type or enzymatic-death mutant TXNDC5 (AAA), FIG. 7C) varies concentrations in assay buffer (100 mM potassium phosphate and 0.2 mM EDTA, pH 7.0). To further validate that the formation of precipitated insulin chain are resulted from catalytic functions of TXNDC5, the 5 μl of $H_2O_2$ in the final concentration 125 mM or 5 μl of 16F16 in the final concentration 50 μM (protein disulfide isomerase inhibitor) is added into 25 μl of reductases/insulin/assay buffer mixture. The 5 μl of 3.5 mM DTT (the final concentration is 0.5 mM) is added into the above mixture to initiate the reaction, and the above reaction is monitored at 650 nm on a Synergy HTX Multi-mode reader (BioTek) for 90 mins at 37° C. The absorbance at 650 nm ($OD_{650nm}$) is measured in 5-min increments throughout 90 mins at 37° C. The accumulated $OD_{650nm}$ is presented as the enzyme kinetic ability.

The LX2 is obtained from Dr. Tung-Hung Su at National Taiwan University Hospital, Taiwan. This cell line is settled in the DMEM containing 10% FBS and 1% penicillin/streptomycin and then is incubated in an incubator with well-controlled of 95% $O_2$ and 5% $CO_2$ circulation at 37° C.

Hydrogen peroxide ($H_2O_2$) is able to halt the reaction by depletion of the reductase. Protein disulfide isomerase inhibitor 16F16 is able to diminish the catalytic activity of TXNDC5.

Meanwhile, further evaluating the influence of TXNDC5 catalytic domain architectures, the fractions of liver cells (Human hepatic stellate cell LX2), transduced with wild-type or enzymatic-death mutant TXNDC5 (AAA) expressed by Lentiviral transduction system, were subjected to the kinetic reduction assay. The kinetic reduction assay is performed referring to the insulin reduction assay described above. Lentiviral transduction system is employed for ectopic expressing control (pLAS2w.pPuro), human wild type (pLAS2w.pPuro-TXNDC5) or enzymatic-death (pLAS2w.pPuro-TXNDC5-AAA) TXNDC5 within interested cell lines with multiplicity of infection (MOI) of 15, and the interested cell lines are harvested for 24 hrs in Polybrene-contained (8 μg/ml), serum-free DMEM media for boosting the desired protein production. After carefully aspirating the old DMEM media and replacing with the fresh DMEM media, the puromycin (0.5 ng/ml) is used to refine the transduced cells for coming processes. Cells are homogenized using 1× Cell Lysis Buffer (Cell Signaling Technology, MA, USA) supplemented with protease inhibitor cocktail and HALT phosphatase inhibitors (Thermo Fisher Scientific, MA, USA), the cells processed as above are then centrifuged at 4° C. for 10 min at 10,000×g, and the supernatant is collected. The concentration of protein lysate is determined by BCA protein assay. A total of 10 μs of each protein sample is diluted in $ddH_2O$ (final volume, 5 μl) for the insulin reduction assay.

Figure 7A:
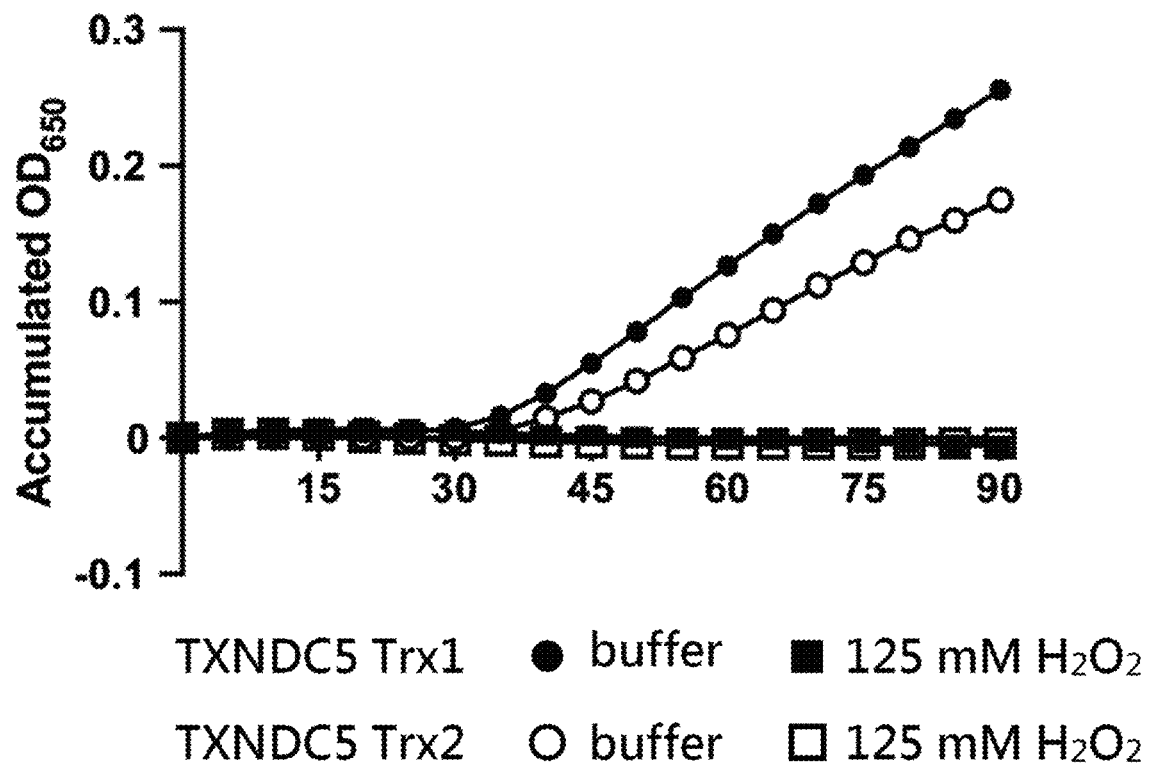
FIG. 7A shows a graph of TXNDC5 disulfide isomerase activity assay by interaction of Trx domain and $H_2O_2$.
Figure 7B:
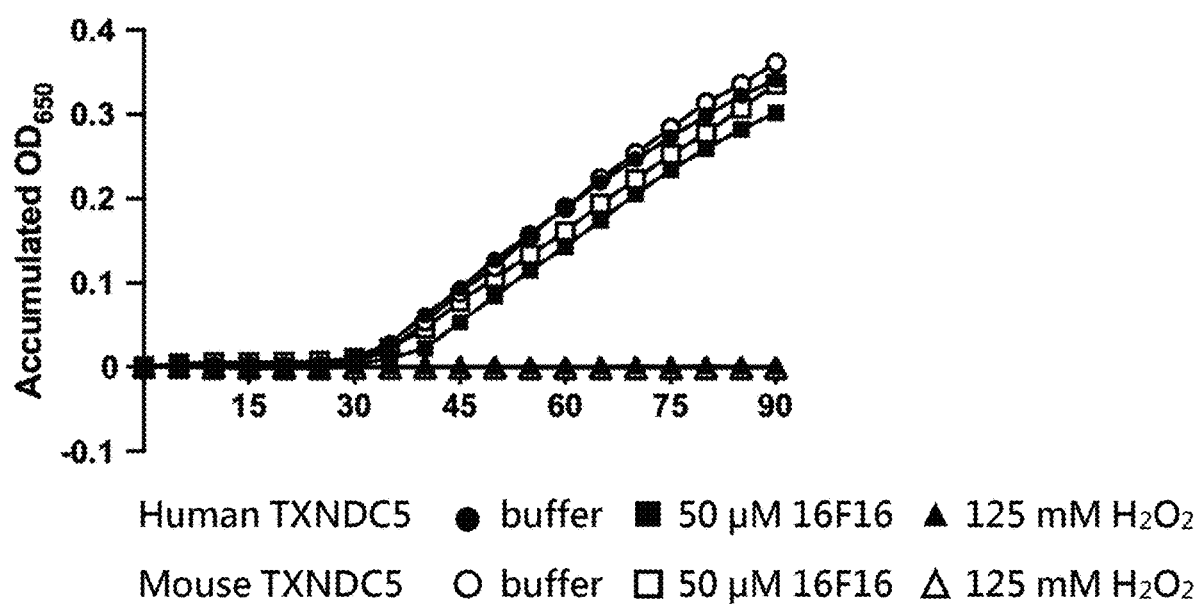
FIG. 7B shows a graph of TXNDC5 disulfide isomerase activity assay by interaction of TXNDC5 and $H_2O_2$ or 16F16.
Figure 7C:
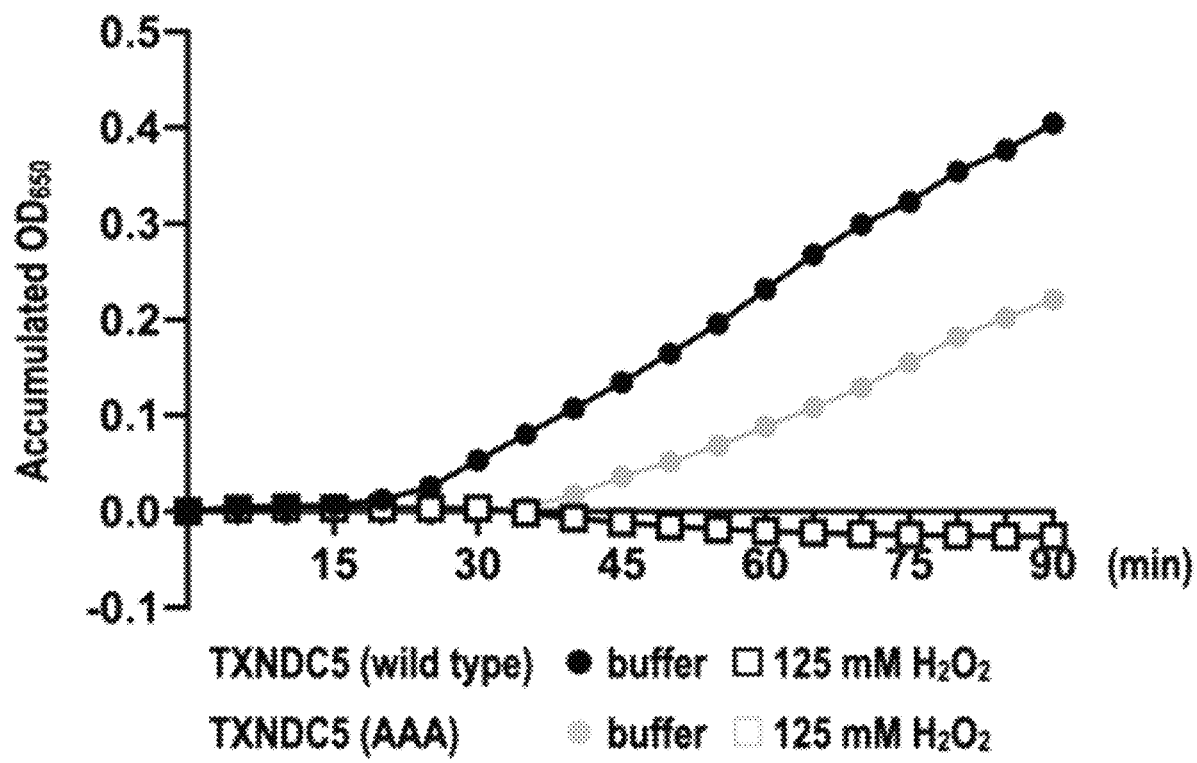
FIG. 7C shows a graph of TXNDC5 disulfide isomerase activity assay by interaction of TXNDC5 expressed by cell and $H_2O_2$.
Figure 8A:
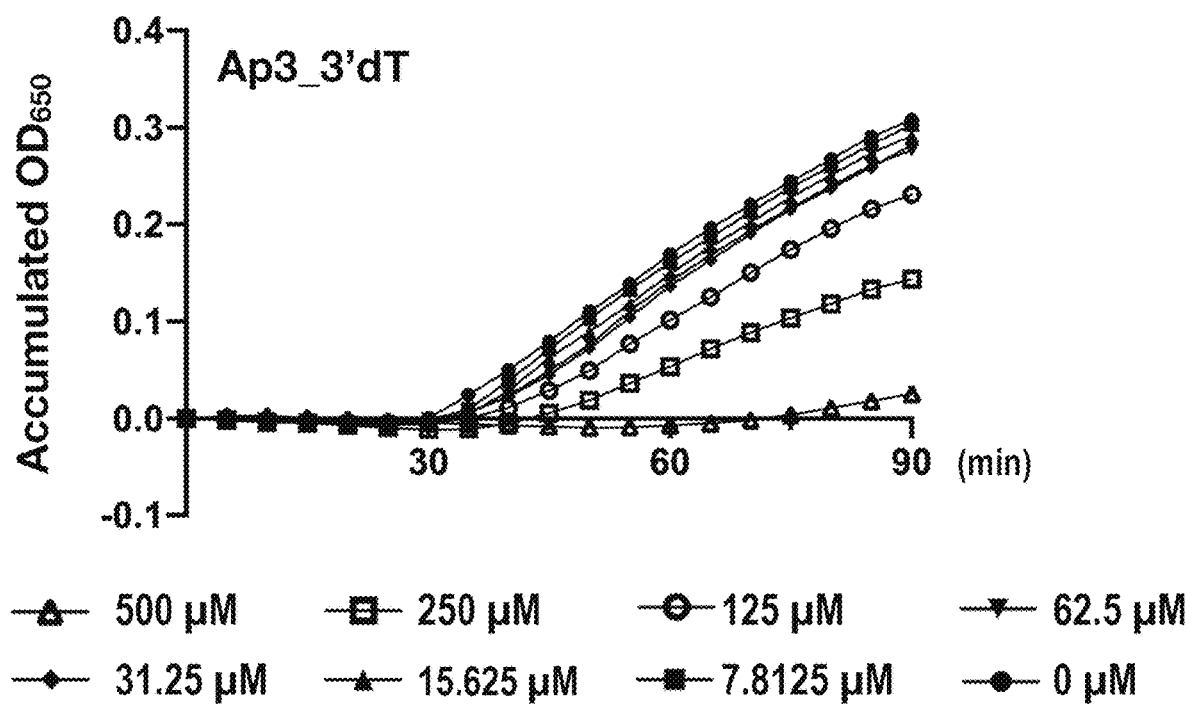
FIG. 8A shows a graph of dose-response assay of aptamer-3.
Figure 8B:
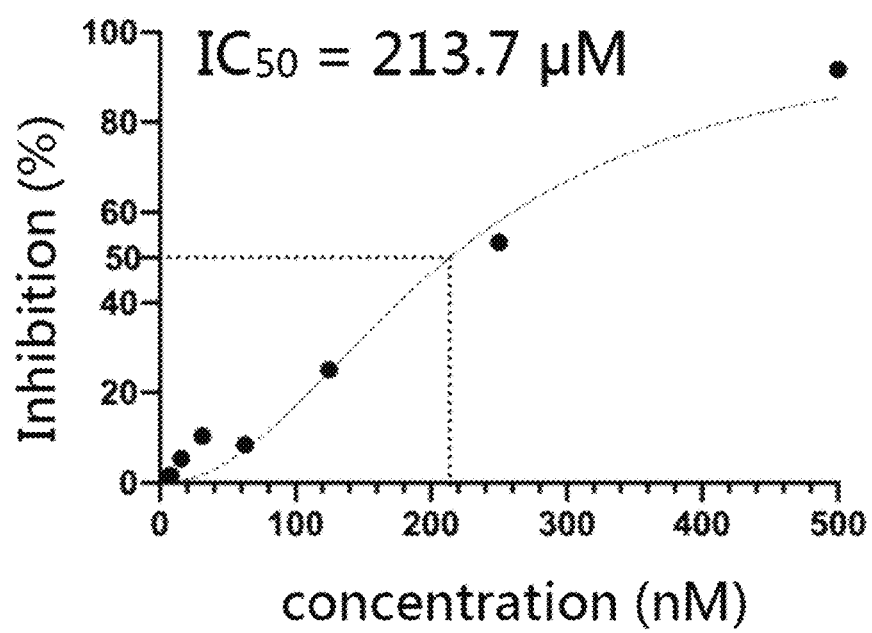
FIG. 8B shows a graph of inhibition rate of aptamer-3.
Figure 8C:
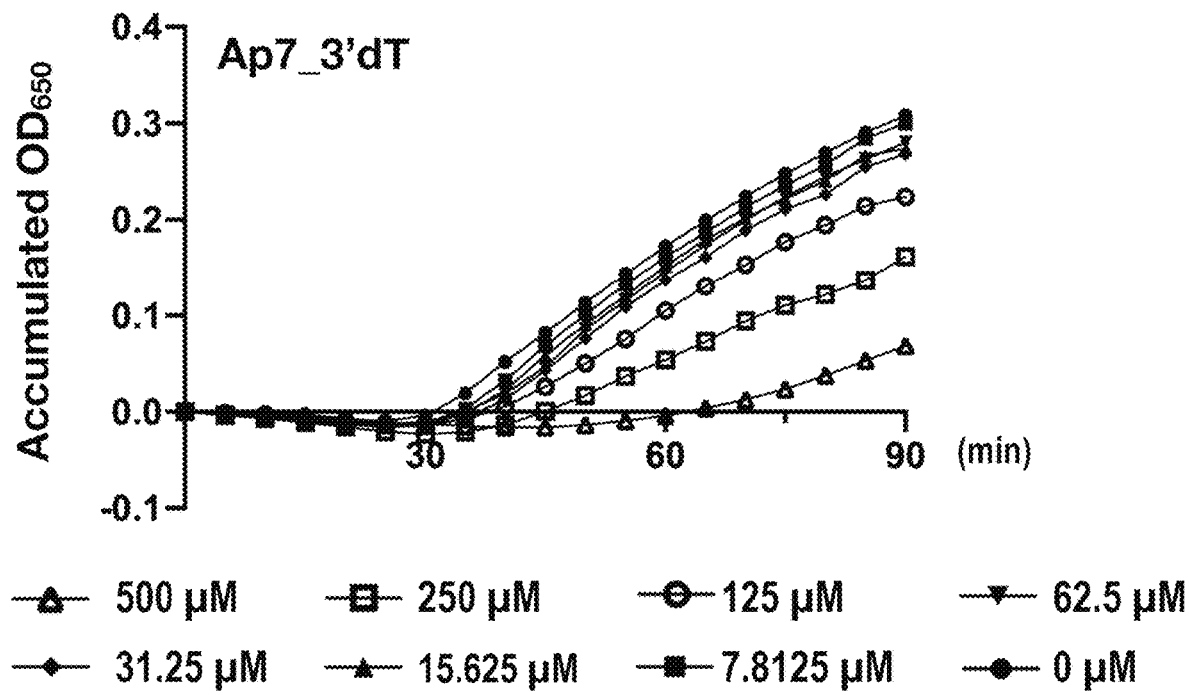
FIG. 8C shows a graph of dose-response assay of aptamer-7.
Figure 8D:
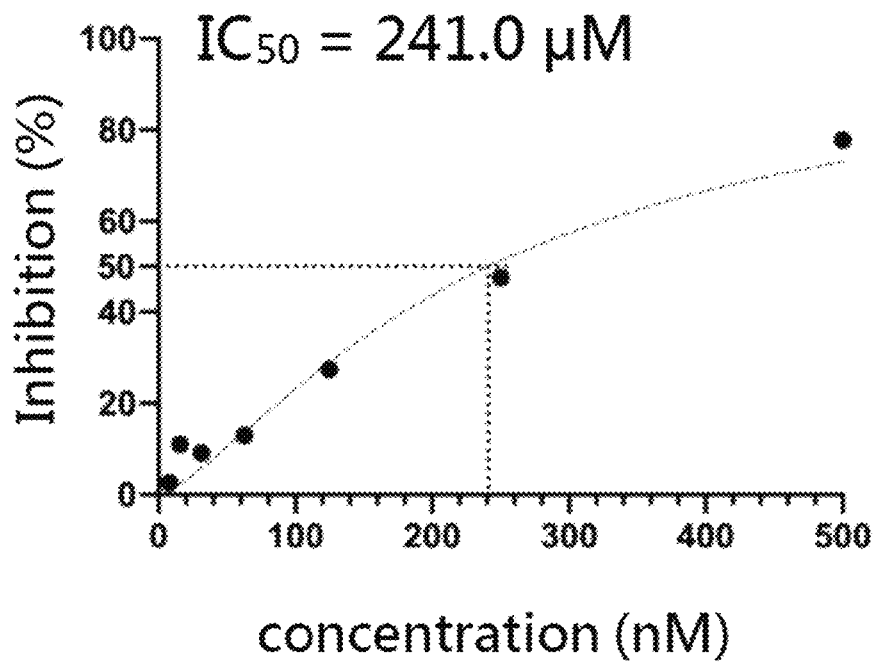
FIG. 8D shows a graph of inhibition rate of aptamer-7.
Figure 8E:
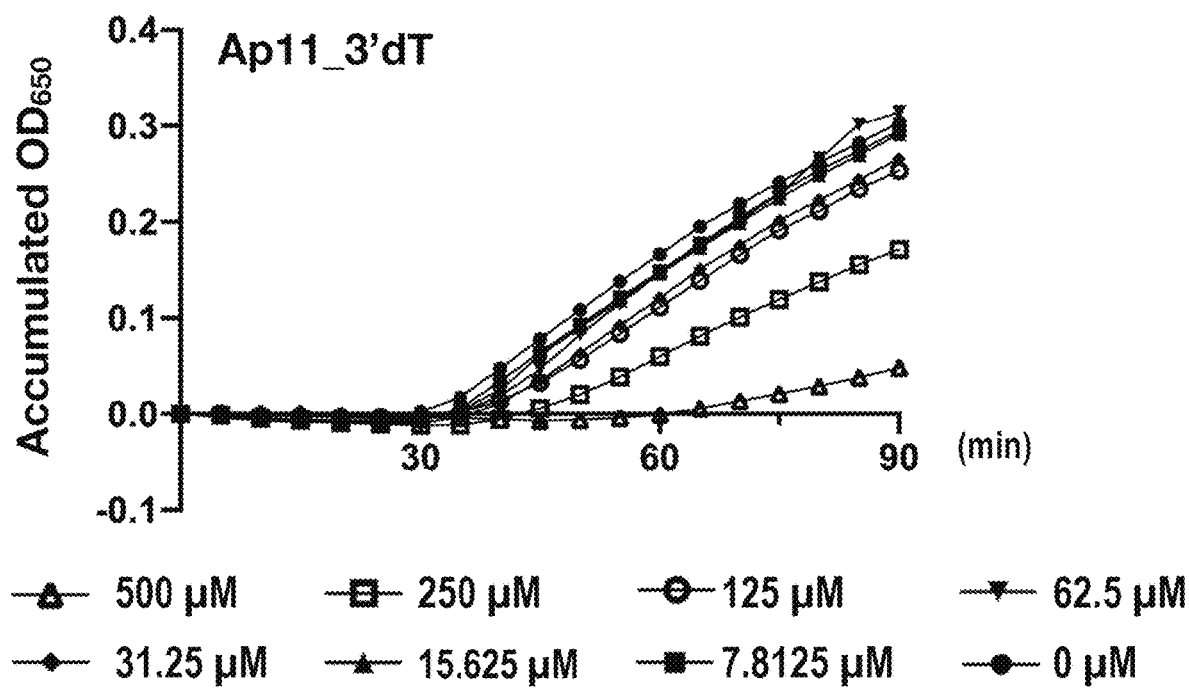
FIG. 8E shows a graph of dose-response assay of aptamer-11.
Figure 8F:
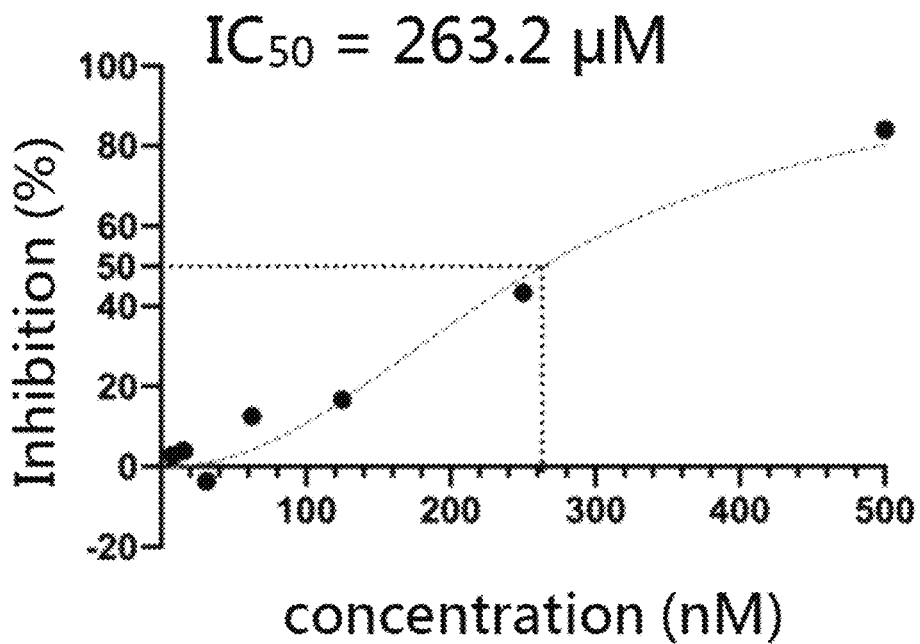
FIG. 8F shows a graph of inhibition rate of aptamer-11.
Figure 9A:
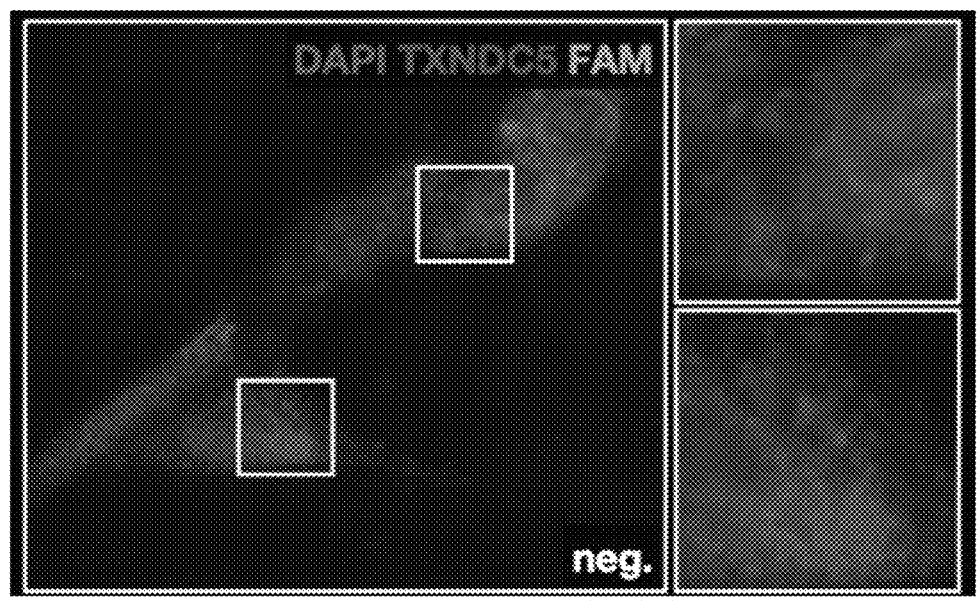
FIG. 9A shows the result of the control group of the in vitro bioactivity assay.
Figure 9B:
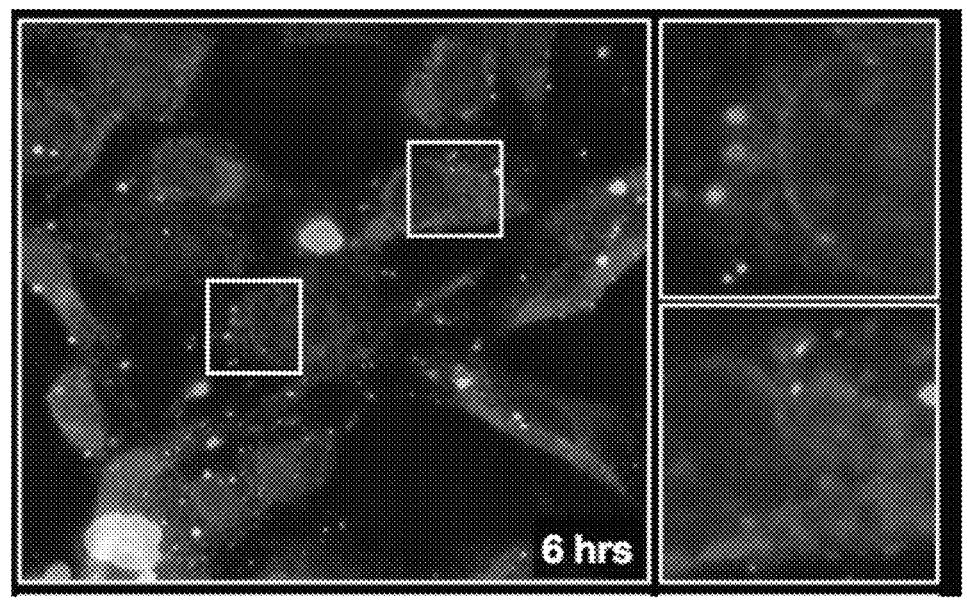
FIG. 9B shows the result of the first experimental group of the in vitro bioactivity assay.
Figure 9C:
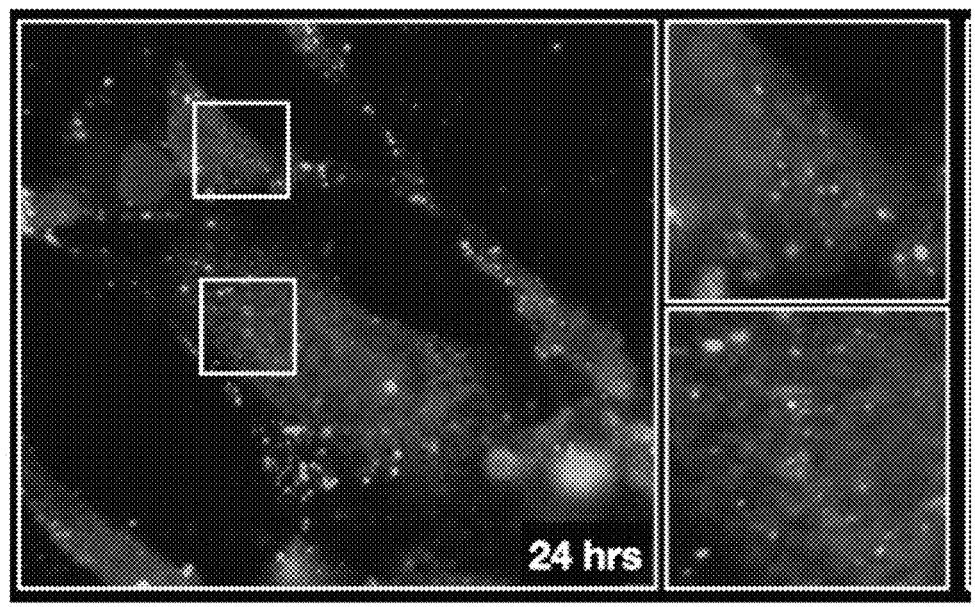
FIG. 9C shows the result of the second experimental group of the in vitro bioactivity assay.
Figure 9D:
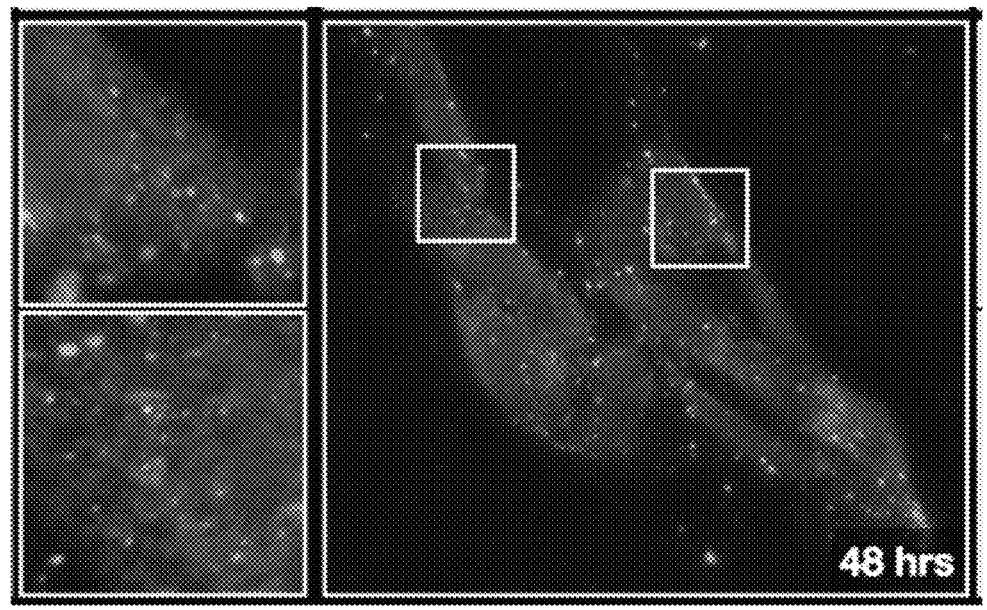
FIG. 9D shows the result of the third experimental group of the in vitro bioactivity assay.

The results of the above reaction of TXNDC5 Trx1 and Trx2 or entire TXNDC5 protein with $H_2O_2$ or 16F16 are shown in FIGS. 7A-7C. The kinetic reactions of both entire TXNDC5 proteins and isolated Trx1 and Trx2 domains with $H_2O_2$ were completely and effectively terminated (FIGS. 7A and B). As shown in FIG. 7B, the plateau of the end-point kinetic absorbance is declined following addition of 16F16, it is demonstrated that the catalytic ability is required for the reductive cleavage of the interchain disulfide bonds in the insulin.

As shown in FIG. 7C, cells with ectopic TXNDC5 expression exhibit higher rate of precipitation of insulin. However, such accelerated reactions were obliterated in the cell lysates containing enzyme-dead mutant TXNDC5 or with the addition of $H_2O_2$.

The procedure for measuring the effects of aptamers (aptamer-3, aptamer-7 and aptamer-11) titration toward TXNDC5 is set forth as following.

Step 1

Each of aptamer-3, aptamer-7 and aptamer-11 (60 μl) are mixed in the binding buffer (20 μl) separately, the mixture of aptamer and the binding buffer is heated to 95° C. for 5 min, snap cooled at 4° C. to form $2^{nd}$ structures, and maintained at 25° C. for 30 min.

Step 2

A half-folded serial dilution of each aptamer mixture is made using 40 μl of the binding buffer as the diluent. Each of aptamer-3, aptamer-7 and aptamer-11 is prepared as various diluents with different concentrations, 7.8125 μM, 15.625 μM, 31.25 μM, 62.5 μM, 125 μM, 250 μM, and 500 μM.

Step 3

Each of 40 μl diluents (with different concentrations, 7.8125 μM, 15.625 μM, 31.25 μM, 62.5 μM, 125 μM, 250 μM, and 500 μM) of aptamer-3, 7 and 11 is incubated with 5 μl human wild type TXNDC5 (0.4 μl human wild type TXNDC5 (3.125 μg/ml) is diluted in 5 μl) for 30 min with vibrating separately.

Step 4

An insulin/assay buffer is prepared by adding 1.6 mM insulin (which is prepared by dissolving insulin in 0.1 N HCl) with the assay buffer consisted of 100 mM potassium phosphate and 0.2 mM EDTA (pH 7). The volume of each insulin/assay buffer is 15 μl, wherein the volume of insulin is 6 μl and the volume of assay buffer is 9 μl.

Step 5

Each of the above mixtures of aptamers (Ap-3, Ap7 and Ap-11) with different concentrations and human wild type TXNDC5 is added with a corresponding insulin/assay buffer separately. That is, aptamer-3, aptamer-7 and aptamer-11 have seven experimental group samples (with different concentrations, 7.8125 μM, 15.625 μM, 31.25 μM, 62.5 μM, 125 μM, 250 μM, and 500 μM) separately. An insulin/assay buffer which is not added with the above mixture of aptamers and human wild type TXNDC5 is prepared as the control group sample.

Step 6

All of the experimental group samples and the control group sample are added at 30 μl per well into a 384-well assay plate. 5 μl of 3.5 mM DTT is subsequently added into each of the experimental group samples and the control group sample and quickly mixed to initiate a reaction.

Step 7

The enzyme reactions of the experimental group samples and the control group sample are monitored at 650 nm on a Synergy HTX Multi-Mode Reader (BioTek).

The results of the enzyme reactions are shown in FIGS. 8A-8F; all three aptamers aptamer-3, aptamer-7 and aptamer-11 inhibited the human TXNDC5 activity in a dose-dependent manner with IC50 values of 213.7 μM for aptamer-3 (B), 241.0 μM for aptamer-7 (D) and 263.2 μM for aptamer-11 (F). It is demonstrated that TXNDC5-targeting aptamers are capable of inhibiting the disulfide isomerase activity of TXNDC5.

In Vitro Bioactivity Assay

For determining the bioactivity of the TXNDC5-targeting DNA aptamers to TXNDC5 in fibroblasts cells, an in vitro bioactivity assay is performed as following.

First, 3T3 cells (ATCC, CRL-1658) are cultured with the cell density of 5,000 cells/cm 2 in the cell culture dish, the 3T3 cells are then suspended in 6,400 μl of Dulbecco's Modified Eagle Medium (DMEM) containing 10% fetal bovine serum (FBS), the 3T3 cells are inoculated in each well of four 8 wells chamber slides (iBidi, 80841), each well contains 200 μl of the above DMEM and 5,000 cells, and the 8 wells chamber slides are placed in an incubator under 37° C. overnight.

On the next day, the medium in each well of each chamber slide is completely suck, and then 100 μl of FBS-free DMEM medium is added into each well of each chamber slide. Afterwards, the 8 wells chamber slides are placed in the incubator under 37° C. for 3 hours. After the 8 wells chamber slides are placed in the incubator under 37° C. for 3 hours, FAM_apt7_dT (the fluorescent protein FAM is conjugated to 5' end of aptamer 7, and 3' end of aptamer 7 is modified with dT) is added into each well of three chamber slide.

Those chamber slides where FAM_apt7_dT has been added into are designated as the first experimental group, the second experimental group and the third experimental group. The chamber slide where FAM_apt7_dT has not been added into is designated as the control group.

After FAM_apt7_dT has been added into the first experimental group for 6 hours, the medium in each well of the first experimental group is completely suck, and the cell fractions in each well of the first experimental group are washed out for 5 minutes by PBS, 4% Paraformaldehyde (PFA) is added into each well of the washed first experimental group for 15 minutes to fix 3T3 cells in each well of the washed first experimental group.

After 4% Paraformaldehyde has been added into the first experimental group for 15 minute, each well of the first experimental group is washed out for 5 minutes by PBS with repeated 3 times and tenfold-diluted permeabilization buffer (Abcam, ab219801) is added into each well of the washed first experimental group for 20 minutes.

After tenfold-diluted permeabilization buffer has been added into the first experimental group for 20 minute, each well of the first experimental group is washed out for 5 minutes by PBS with repeated 3 times and 200 μl/well of 5% bovine serum albumin (BioFroxx) blocking buffer is added into each well of the washed first experimental group for 1 hour at room temperature.

After 200 μl/well of 5% bovine serum albumin (BioFroxx) blocking buffer has been added into the first experimental group for 1 hour, each well of the first experimental group is washed out for 5 minutes by PBS with repeated 3 times and primary antibody, TXNDC5 polyclonal antibody (Proteintech, 19834-1-AP) (diluted with the blocking buffer in a 1:100 dilution) is added into each well of the washed first experimental group (the final concentration of TXNDC5 polyclonal antibody is 6.5 μg/ml) overnight at 4° C.

After TXNDC5 polyclonal antibody has been added into the first experimental group overnight, each well of the first experimental group is washed out for 5 minutes by PBS with repeated 3 times and secondary antibody, donkey anti-rabbit, Alexa Flour 555 (Invitrogen, A-31572) (diluted with the blocking buffer in a 1:500 dilution) is added into each well of the washed first experimental group (the final concentration of secondary antibody is 4 μg/ml) for 2 hours at room temperature, thereby TXNDC5 in the first experimental group is labeled.

After the secondary antibody has been added into the first experimental group for 2 hours, each well of the first experimental group is washed out for 5 minutes by PBS with repeated 3 times, the liquid left over in each well of the washed first experimental group (main liquid is PBS) is further removed. After the liquid left over in the first experimental group is removed, the mounting medium (Southern Biotech, 0100-20) which contains 4',6-diaminndino-2-phenylinndole (DAPI) is used for labeling the nucleus of 3T3 cells in the first experimental group.

The image of the stained 3T3 cells is taken by the fluorescence microscope EVOS M7000 (Invitrogen).

The above in vitro bioactivity assay is repeated two times.

The second experimental group, the third experimental group and the control repeat the process procedure as the first experimental group as mentioned above. The only different experimental condition between the first experimental group, the second experimental group, the third experimental group and the control group is the reaction time when FAM_apt7_dT has been added into the first experimental group, the second experimental group or the third experimental group. FAM_apt7_dT has been added into the second experimental group for 24 hours, FAM_apt7_dT has been added into the third experimental group for 48 hours, and FAM_apt7_dT has not been added into the control group.

The results of the in vitro bioactivity assay are shown in FIGS. 9A-9D. FAM' labeled DNA aptamers (green-colored) were uptaken by 3T3 cells from 6 hr, colocalized with TXNDC5 (red-colored) and remained detectable in the cytoplasm at 48 hr. The results of FIGS. 9A-9D reveal that these DNA aptamers can be freely uptaken by fibroblasts and interact with TXNDC5. Meanwhile, the intracellular stability of these DNA aptamers could be maintained for at least 48 hours The above results also suggest that DNA aptamers could directly interact with TXNDC5 without any adjuvant.

Anti-Fibrotic Effects Assay

For determining the anti-fibrotic effects of the TXNDC5-targeting DNA aptamers in fibroblasts cells, an anti-fibrotic effects assay is performed as following.

First, 3T3 cells (ATCC, CRL-1658) are cultured with the cell density of cells/cm 2 in the cell culture dish, the 3T3 cells are then suspended in 3,200 μl of Dulbecco's Modified Eagle Medium(DMEM) containing 10% fetal bovine serum (FBS), the 3T3 cells are inoculated in each well of two 8 wells chamber slides (iBidi, 80841), each well contains 200

μl of the above DMEM and 5,000 cells, and the 8 wells chamber slides are placed in an incubator under 37° C. overnight. One of the chamber slides is designated as the 24-hrs group, every two wells of the 24-hrs group are designated as the first experimental group, the second experimental group, the third experimental group and the control group separately. Another chamber slide is designated as the 48-hrs group, the 48-hrs group also has the first experimental group, the second experimental group, the third experimental group and the control group as the 24-hrs group.

On the next day, the medium in each well of the 24-hrs group and the 48-hrs group is completely suck, and then 50 μl of FBS-free DMEM medium is added into each well of the 24-hrs group and the 48-hrs group. Afterwards, the 24-hrs group and the 48-hrs group are placed in the incubator under 37° C. for 3 hours. After the 24-hrs group and the 48-hrs group are placed in the incubator under 37° C. for 3 hours, TGFβ (final dose: 10 μg/ml) is added into each well of the first experimental group of the 24-hrs group and the 48-hrs group; TGFβ (final dose: 10 μg/ml) and non-targeting aptamer (Spt_dT) (final dose: 5 μg/ml) are added together into each well of the second experimental group of the 24-hrs group and the 48-hrs group; TGFβ (final dose: 10 μg/ml) and FAM_apt7_dT aforementioned (final dose: 5 μg/ml) are added together into each well of the third experimental group of the 24-hrs group and the 48-hrs group; nothing is added into each well of the control group of the 24-hrs group and the 48-hrs group.

After the first experimental group, the second experimental group, the third experimental group and the control group of the 24-hrs group is treated as mentioned above for 24 hours, the medium in each well of the 24-hrs group is completely suck, and the cell fractions in each well of the 24-hrs group are washed out for 5 minutes by PBS, 4% PFA is added into each well of the washed 24-hrs group for 15 minutes to fix 3T3 cells in each well of the washed 24-hrs group.

After 4% PFA has been added into the 24-hrs group for 15 minute, each well of the 24-hrs group is washed out for 5 minutes by PBS with repeated 3 times and tenfold-diluted permeabilization buffer (Abcam, ab219801) is added into each well of the washed 24-hrs group for 20 minutes.

After tenfold-diluted permeabilization buffer has been added into the 24-hrs group for 20 minute, each well of the 24-hrs group is washed out for 5 minutes by PBS with repeated 3 times and 200 μl/well of 5% bovine serum albumin (BioFroxx) blocking buffer is added into each well of the washed 24-hrs group for 1 hour at room temperature.

After 200 μl/well of 5% bovine serum albumin (BioFroxx) blocking buffer has been added into the 24-hrs group for 1 hour, each well of the 24-hrs group is washed out for 5 minutes by PBS with repeated 3 times and primary antibody, αsmooth actin (αSMA) polyclonal antibody (Abcam, ab5694) (diluted with the blocking buffer in a 1:100 dilution) is added into each well of the washed 24-hrs group (the final concentration of αSMA polyclonal antibody is 2 μg/ml) overnight at 4° C.

After αSMA polyclonal antibody has been added into the 24-hrs group overnight, each well of the 24-hrs group is washed out for 5 minutes by PBS with repeated 3 times and secondary antibody, donkey anti-rabbit, Alexa Flour 555 (Invitrogen, A-31572) (diluted with the blocking buffer in a 1:500 dilution) is added into each well of the washed 24-hrs group (the final concentration of secondary antibody is 4 μg/ml) for 2 hours at room temperature, thereby αSMA in the 24-hrs group is labeled.

After the secondary antibody has been added into the 24-hrs group for 2 hours, each well of the 24-hrs group is washed out for 5 minutes by PBS with repeated 3 times, the liquid left over in each well of the washed 24-hrs group (main liquid is PBS) is further removed. After the liquid left over in the 24-hrs group is removed, the mounting medium (Southern Biotech, 0100-20) which contains DAPI is used for labeling the nucleus of 3T3 cells in the 24-hrs group.

The image of the stained 3T3 cells in the 24-hrs group is taken by the fluorescence microscope EVOS M7000 (Invitrogen).

The above anti-fibrotic effects assay in the 24-hrs group is repeated three times.

The 48-hrs group repeats the process procedure as the 24-hrs group as mentioned above. The only different experimental condition between the 24-hrs group and the 48-hrs group is the reaction when TGFβ, FAM_apt7_dT, Spt_dT or their combination have been added into the 24-hrs group and the 48-hrs group. The reaction time of the 24-hrs group is 24 hours, and the reaction time of the 48-hrs group is 48 hours.

Figure 10A:
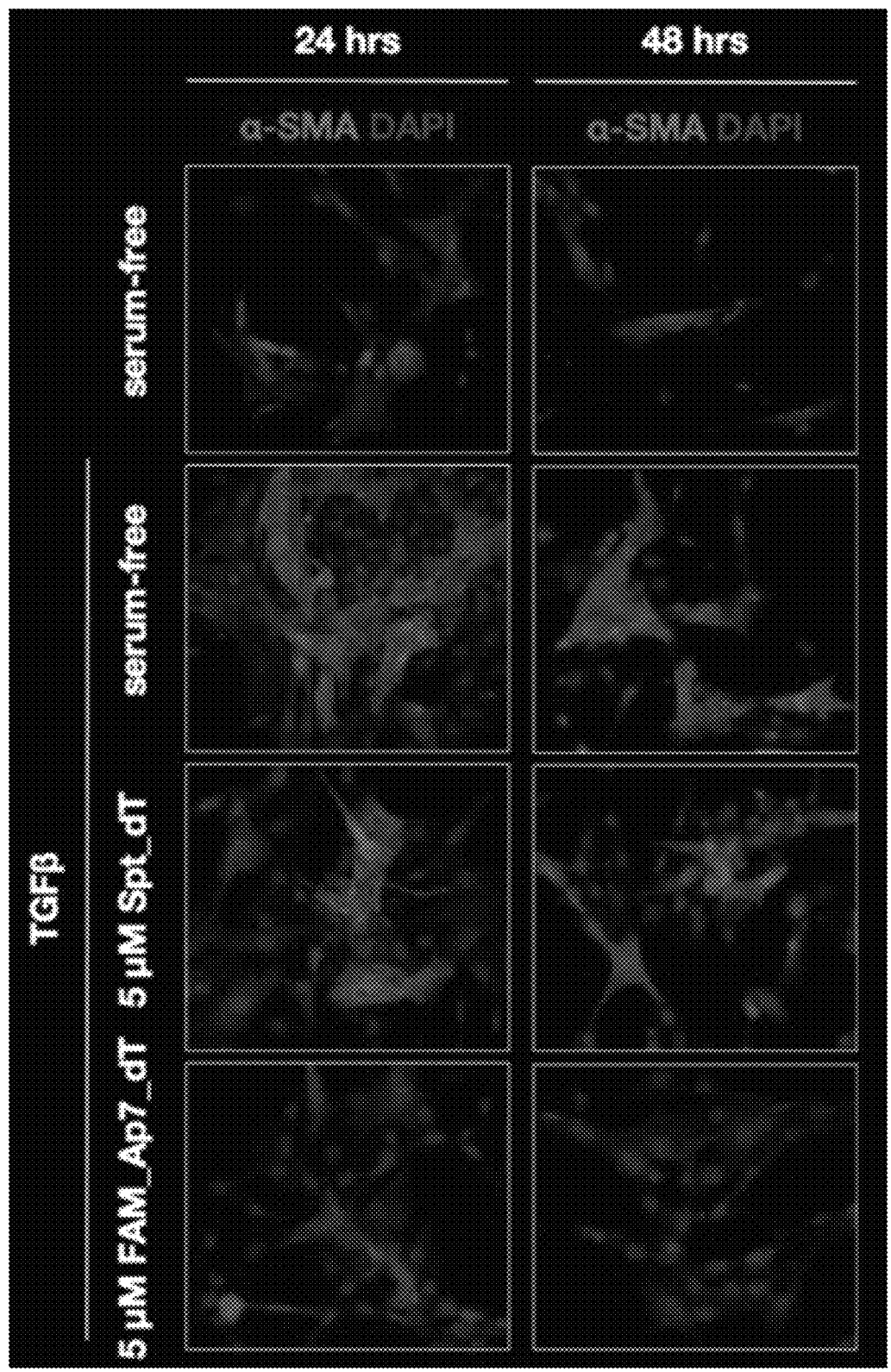
FIG. 10A shows the result of the anti-fibrotic effects assay.
Figure 10B:
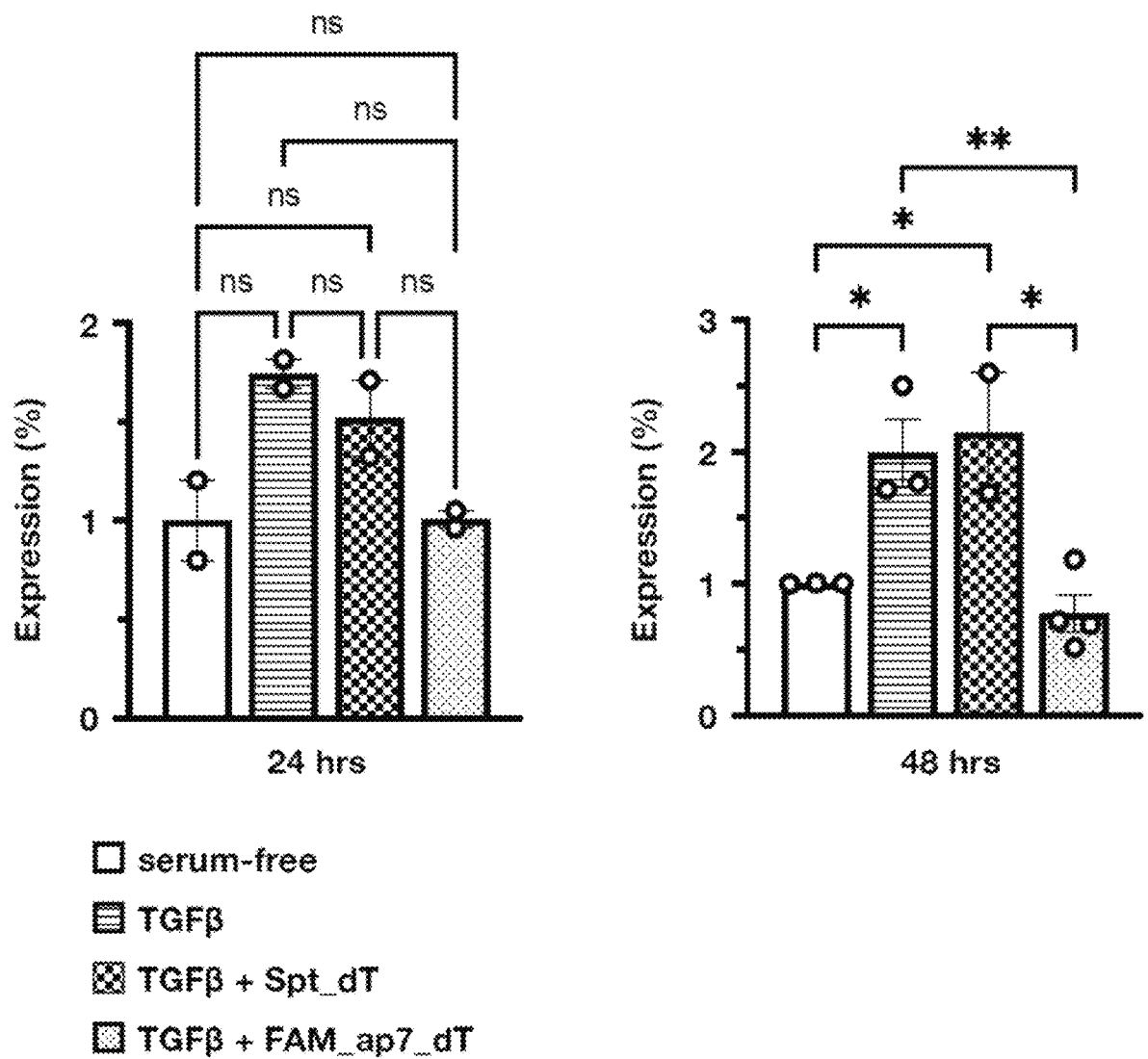
FIG. 10B shows the result of the anti-fibrotic effects assay.

The results of the anti-fibrotic effects assay are shown in FIGS. 10A and 10B. FIG. 10A shows that aptamer 7 inhibits the expression of αSMA which is a marker for fibroblast activation and myofibroblast transdifferentiation in 3T3 fibroblast cells treated with TGFβ stimulation. Compared with the control group, the first experimental group (TGFβ-only group) and the second experimental group (Spt_dT group) significantly express αSMA in 3T3 cells at both 24th and 48th hour, but the third experimental group (FAM_Ap7_dT group) significantly suppresses αSMA in 3T3 cells at both 24th and 48th hour. FIG. 10B shows the αSMA expression rates of the first experimental group, the second experimental group and the third experimental group, the symbol "ns" in FIG. 10B means that the data is non-significant, the asterisk in FIG. 10B means P value (* $P<0.05$, ** $P<0.01$).

The treatment of TXNDC5-targeting DNA aptamer (FAM_Apt_dT), but not non-targeting aptamer (Spt_dT), markedly repressed αSMA expression in 3T3 cells in response to TGFβ stimulation, both at 24 and 48 hr.

In-Cell Western Assay

For determining the inhibitory effect of TXNDC5-targeting DNA aptamer on the cellular expression levels of fibronectin, an in-cell Western assay is performed as following.

First, 3T3 cells (ATCC, CRL-1658) are cultured with the cell density of 5,000 cells/cm 2 in the cell culture dish, the 3T3 cells are then suspended in 4,800 μl of Dulbecco's Modified Eagle Medium(DMEM) containing 10% fetal bovine serum (FBS), the 3T3 cells are inoculated in 64 wells of a 96 wells plate, each well contains 100 μl of the above DMEM and 1,600 cells, and the 96 wells plate is placed in an incubator under 37° C. overnight.

At the same time, the aptamer for the present in-cell Western assay is prepared. The preparing process of the aptamer is performing as following. 15.75 μl of FAM_apt_dT stock (100 μM), 1 μl of Tris-Cl (400 mM), 2 μl of NaCl (1.5 μM), 1 μl of KCl (1 μM), 0.04 μl of $MgCl_2$ (1 μM), 0.2 μl of $CaCl_2$ (100 mM) and 0.01 μl of Tween-20 are mixed. The final volume of the above mixture is 20 μl, and the concentration of FAM_apt_dT in the mixture is 78.75 μM. The mixture is then heated to 95° C. for 5 minutes. After the mixture is heated for 5 minutes, the mixture is cooled down at 4° C. for 30 sec and then placed under 25° C. for 30 minutes to make the aptamer folded. FAM_apt_dT stock at a concentration of 78.75 μM is prepared according to the above process. For obtaining the FAM_apt_dT solution at different concentrations, 70 µl of FAM_apt_dT stock (78.75 µM) is mixed with 70 µl of the binding solution to prepare FAM_apt_dT solution at a concentration of 39.375 µM, the FAM_apt_dT solution at the concentration of 39.375 µM is then sequentially diluted according to the previous manner to prepare FAM_apt_dT solution at a concentration of 19.68 µM, 9.84 µM, 4.92 µM, 2.4604 and 1.23 µM separately.

On the next day, the medium in the 64 wells of the above 96 wells plate is completely suck, and then 50 µl of FBS-free DMEM medium is added into each of the above 64 wells. Afterwards, the above 96 wells plate is placed in the incubator under 37° C. for 3 hours. After the above 96 wells plate has been placed in the incubator under 37° C. for 3 hours, the 64 wells of the above 96 wells plate are treated with different conditions. 32 wells of the above 96 wells plate are designated as the control group, the 3T3 cells of the control group are not treat with TGFβ. The other 32 wells of the 96 wells plate are designated as the experimental group, the 3T3 cells of the experimental group are treat with 10 µg/ml of TGFβ. Both the experimental group and the control group (which contains 50 µl of FBS-free DMEM medium) are treated with FAM_apt_dT as following.

70 µl of FAM_apt_dT at the concentration of 78.75 µM is added into each of the first four wells of the experimental group/the control group contain (the final concentration of FAM_apt_dT is 20 µM); 70 µl of FAM_apt_dT at the concentration of 39.375 µM is added into each of the second four wells of the experimental group/the control group (the final concentration of FAM_apt_dT is 10 µM); 70 µl of FAM_apt_dT at the concentration of 19.68 µM is added into each of the third four wells of the experimental group/the control group (the final concentration of FAM_apt_dT is 5 µM); 70 µl of FAM_apt_dT at the concentration of 9.84 µM is added into each of the fourth four wells of the experimental group/the control group (the final concentration of FAM_apt_dT is 2.5 µM); 70 µl of FAM_apt_dT at the concentration of 4.92 µM is added into each of the fifth four wells of the experimental group/the control group (the final concentration of FAM_apt_dT is 1.25 µM); 70 µl of FAM_apt_dT at the concentration of 2.46 µM is added into each of the six four wells of the experimental group/the control group (the final concentration of FAM_apt_dT is 0.625 µM); 70 µl of FAM_apt_dT at the concentration of 1.23 µM is added into each of the seventh four wells of the experimental group/the control group (the final concentration of FAM_apt_dT is 0.3125 µM); each of the eighth four wells of the experimental group/the control group does not added with FAM_apt_dT.

After the experimental group and the control group have been treated as above, the experimental group and the control group are then placed in the incubator under 37° C. for 72 hours.

After the experimental group and the control group have been placed in the incubator for 72 hours, the medium in each well of the experimental group and the control group is completely suck, the cell fractions in each well of the experimental group and the control group are washed out for 5 minutes by PBS with repeated 3 times, and then 4% PFA is added into each well of the washed experimental group and the washed control group for 20 minutes to fix 3T3 cells in each well of the experimental group and the control group.

After 4% PFA has been added into the experimental group and the control group for 20 minute, each well of the experimental group and the control group is washed out for 5 minutes by PBS with repeated 3 times, and tenfold-diluted permeabilization buffer (Abcam, ab219801) is added into each well of the washed experimental group and the washed control group for 20 minutes.

After tenfold-diluted permeabilization buffer has been added into the experimental group and the control group for 20 minute, each well of the experimental group and the control group is washed out for 5 minutes by PBS with repeated 3 times and 150 µl/well of LI-COR blocking buffer is added into each well of the experimental group and the control group for 1 hour at room temperature.

After 150 µl/well of LI-COR blocking buffer has been added into the experimental group and the control group for 1 hour, each well of the experimental group and the control group is washed out for 5 minutes by PBS with repeated 3 times and primary antibody, fibronectin monoclonal antibody (BD Biosciences, 610077) (diluted with the LI-COR blocking buffer in a 1:100 dilution) is added into each well of the experimental group and the control group (the final concentration of fibronectin monoclonal antibody is 2.5 µg/ml) overnight at 4° C.

After fibronectin monoclonal antibody has been added into the experimental group and the control group overnight, each well of the experimental group and the control group overnight is washed out for 5 minutes by PBS with repeated 3 times. Afterward, secondary antibody, goat-anti Mouse IRDye 800CW (diluted with the LI-COR blocking buffer in a 1:1000 dilution) and Celltag 700 (diluted with the LI-COR blocking buffer in a 1:500 dilution) are together added into each well of the experimental group and the control group (the final concentration of secondary antibody is 1 µg/ml, the final concentration of Celltag 700 is 0.2 µg/ml) for 2 hours at room temperature, thereby fibronectin and the number of 3T3 cells in the experimental group and the control group is detected. The experimental group and the control group are scanned and analyzed by Odyssey CLx infrared imaging system. $IC_{50}$ of the experimental group and the control group are calculated by Prism.

Figure 11A:
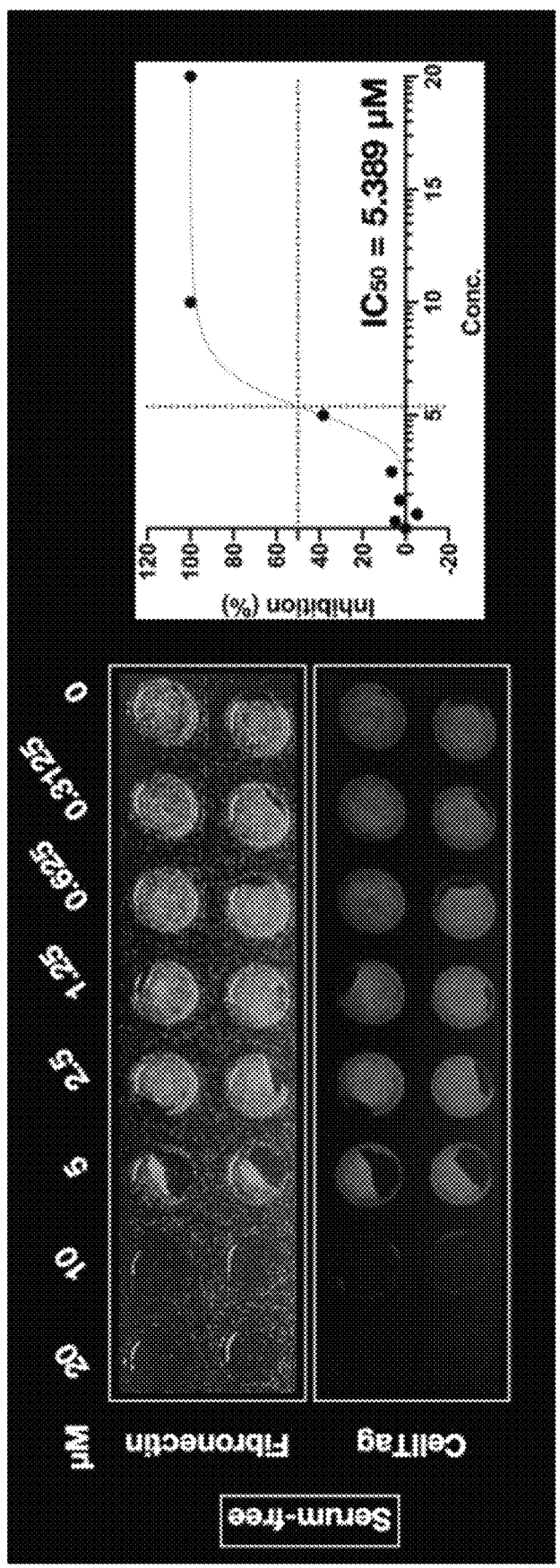
FIG. 11A shows the result of the in-cell Western assay.
Figure 11B:
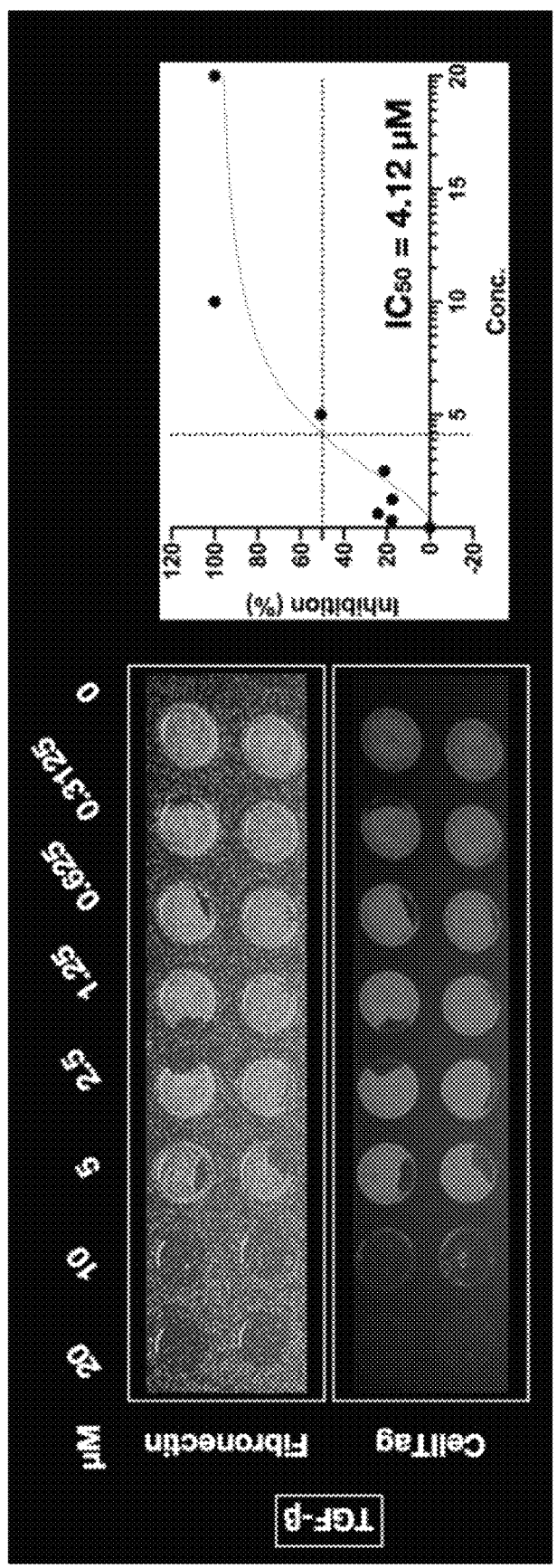
FIG. 11B shows the result of the in-cell Western assay.

The results of the in-cell Western assay are shown in FIGS. 11A and 11B. FIGS. 11A and 11B shows that a strong inhibitory effect of TXNDC5-targeting DNA aptamer on the cellular expression levels of fibronectin, a critical ECM protein during fibrogenesis, either without TGFβ ($IC_{50}$ 5.389 µM) or with TGFβ ($IC_{50}$ 4.12 µM) stimulation.

As disclosed above, TXNDC5-targeting aptamers are capable of binding with TXNDC5 protein and inhibiting the catalytic ability of TXNDC5. The previous studies also identified that targeting TXNDC5 is an effective therapeutic approach to prevent or treat organ fibrosis (such as cardiac fibrosis, liver fibrosis, renal fibrosis and pulmonary fibrosi), heart failure and chronic kidney diseases. Therefore, a pharmaceutical composition comprising the TXNDC5-targeting aptamers as an active ingredient is able to be utilized to prevent or treat organ fibrosis, heart failure and chronic kidney diseases. The above pharmaceutical composition may further comprise a pharmaceutically acceptable carrier, such as normal saline, nanoparticles or any known carrier suitable for aptamers.

Meanwhile, a method for preventing or treating organ fibrosis can be provided, the method comprises administering an effective amount of the TXNDC5-targeting aptamer to a subject in need thereof.

While the present disclosure has been described by means of specific embodiments, numerous modifications and variations could be made thereto by those skilled in the art without departing from the scope and spirit of the present disclosure set forth in the claims.

What is claimed is:

1. A DNA aptamer comprising a polynucleotide specifically binding to TXNDC5, wherein the polynucleotide is selected from the group consisting of the nucleotide sequence of any one of SEQ ID NOS: 1-14.

2. The DNA aptamer of claim 1, wherein the polynucleotide is the nucleotide sequence of SEQ ID NOS: 3.

3. The DNA aptamer of claim 1, wherein the polynucleotide is the nucleotide sequence of SEQ ID NOS: 7.

4. The DNA aptamer of claim 1, wherein the polynucleotide is the nucleotide sequence of SEQ ID NOS: 11.

5. A pharmaceutical composition comprising the DNA aptamer of claim 1 as an active ingredient.

6. The pharmaceutical composition of claim 5, wherein the DNA aptamer is a therapeutic agent against cardiac fibrosis.

7. The pharmaceutical composition of claim 5, wherein the DNA aptamer is a therapeutic agent against heart failure.

8. The pharmaceutical composition of claim 5, wherein the DNA aptamer is a therapeutic agent against liver fibrosis.

9. The pharmaceutical composition of claim 5, wherein the DNA aptamer is a therapeutic agent against renal fibrosis.

10. The pharmaceutical composition of claim 5, wherein the DNA aptamer is a therapeutic agent against chronic kidney diseases.

11. The pharmaceutical composition of claim 5, wherein the DNA aptamer is a therapeutic agent against pulmonary fibrosis.

12. A method for inhibiting the catalytic ability of TXNDC5, comprising binding the aptamer of claim 1 to TXNDC5.

* * * * *

SEQUENCE LISTING

<160> NUMBER OF SEQ ID NOS: 18

<210> SEQ ID NO 1
<211> LENGTH: 50
<212> TYPE: DNA
<213> ORGANISM: Artificial Sequence
<220> FEATURE:
<223> OTHER INFORMATION: Aptamer

<400> SEQUENCE: 1
agcagcacag aggtctagat gtaaaggtac ctcaggcgtg ctaccgtgaa          50

<210> SEQ ID NO 2
<211> LENGTH: 50
<212> TYPE: DNA
<213> ORGANISM: Artificial Sequence
<220> FEATURE:
<223> OTHER INFORMATION: Aptamer

<400> SEQUENCE: 2
agcagcacag aggtcccttt aaggcttttg gtccggcgtg ctaccgtgaa          50

<210> SEQ ID NO 3
<211> LENGTH: 50
<212> TYPE: DNA
<213> ORGANISM: Artificial Sequence
<220> FEATURE:
<223> OTHER INFORMATION: Aptamer

<400> SEQUENCE: 3
agcagcacag aggtcaatgt aatctttatc tatcggcgtg ctaccgtgaa          50

<210> SEQ ID NO 4
<211> LENGTH: 50
<212> TYPE: DNA
<213> ORGANISM: Artificial Sequence
<220> FEATURE:
<223> OTHER INFORMATION: Aptamer

<400> SEQUENCE: 4
agcagcacag aggtctcgtt ttactctcgt gtttggcgtg ctaccgtgaa          50

<210> SEQ ID NO 5
<211> LENGTH: 50
<212> TYPE: DNA
<213> ORGANISM: Artificial Sequence
<220> FEATURE:
<223> OTHER INFORMATION: Aptamer

<400> SEQUENCE: 5
agcagcacag aggtcatcat ctggactcgg aatcggcgtg ctaccgtgaa          50

<210> SEQ ID NO 6
<211> LENGTH: 50
<212> TYPE: DNA
<213> ORGANISM: Artificial Sequence
<220> FEATURE:
<223> OTHER INFORMATION: Aptamer

<400> SEQUENCE: 6
agcagcacag aggtcggtgt atgactttat ttccggcgtg ctaccgtgaa          50

<210> SEQ ID NO 7
<211> LENGTH: 50
<212> TYPE: DNA
<213> ORGANISM: Artificial Sequence -continued
<220> FEATURE:
<223> OTHER INFORMATION: Aptamer

<400> SEQUENCE: 7
agcagcacag aggtcaggaa ccttatgcct atgtagcgtg ctaccgtgaa        50

<210> SEQ ID NO 8
<211> LENGTH: 50
<212> TYPE: DNA
<213> ORGANISM: Artificial Sequence
<220> FEATURE:
<223> OTHER INFORMATION: Aptamer

<400> SEQUENCE: 8
agcagcacag aggtccctat caaccacacc atcttgcgtg ctaccgtgaa        50

<210> SEQ ID NO 9
<211> LENGTH: 50
<212> TYPE: DNA
<213> ORGANISM: Artificial Sequence
<220> FEATURE:
<223> OTHER INFORMATION: Aptamer

<400> SEQUENCE: 9
agcagcacag aggtctattg tgaactttt cagcggcgtg ctaccgtgaa         50

<210> SEQ ID NO 10
<211> LENGTH: 50
<212> TYPE: DNA
<213> ORGANISM: Artificial Sequence
<220> FEATURE:
<223> OTHER INFORMATION: Aptamer

<400> SEQUENCE: 10
agcagcacag aggtccctct ccggtatgct tatttgcgtg ctaccgtgaa        50

<210> SEQ ID NO 11
<211> LENGTH: 50
<212> TYPE: DNA
<213> ORGANISM: Artificial Sequence
<220> FEATURE:
<223> OTHER INFORMATION: Aptamer

<400> SEQUENCE: 11
agcagcacag aggtctctta ttactctccc gtaccgcgtg ctaccgtgaa        50

<210> SEQ ID NO 12
<211> LENGTH: 50
<212> TYPE: DNA
<213> ORGANISM: Artificial Sequence
<220> FEATURE:
<223> OTHER INFORMATION: Aptamer

<400> SEQUENCE: 12
agcagcacag aggtcgactc ttgatttcct tgcatgcgtg ctaccgtgaa        50

<210> SEQ ID NO 13
<211> LENGTH: 50
<212> TYPE: DNA
<213> ORGANISM: Artificial Sequence
<220> FEATURE:
<223> OTHER INFORMATION: Aptamer

<400> SEQUENCE: 13
agcagcacag aggtcgactc ttgatttcct tgcatgcgtg ctaccgtgaa        50

```
<210> SEQ ID NO 14
<211> LENGTH: 50
<212> TYPE: DNA
<213> ORGANISM: Artificial Sequence
<220> FEATURE:
<223> OTHER INFORMATION: Aptamer

<400> SEQUENCE: 14
agcagcacag aggtcattcg attgttttac aatttgcgtg ctaccgtgaa            50

<210> SEQ ID NO 15
<211> LENGTH: 15
<212> TYPE: DNA
<213> ORGANISM: Artificial Sequence
<220> FEATURE:
<223> OTHER INFORMATION: Primer

<400> SEQUENCE: 15
agcagcacag aggtc                                                  15

<210> SEQ ID NO 16
<211> LENGTH: 15
<212> TYPE: DNA
<213> ORGANISM: Artificial Sequence
<220> FEATURE:
<223> OTHER INFORMATION: Primer

<400> SEQUENCE: 16
ttcacggtag cacgc                                                  15

<210> SEQ ID NO 17
<211> LENGTH: 108
<212> TYPE: PRT
<213> ORGANISM: Homo sapiens
<220> FEATURE:
<223> OTHER INFORMATION: TXNDC5 Trx1

<400> SEQUENCE: 17
```

Ser Lys His Leu Tyr Thr Ala Asp Met Phe Thr His Gly Ile Gln Ser
1               5                   10                  15

Ala Ala His Phe Val Met Phe Phe Ala Pro Trp Cys Gly His Cys Gln
            20                  25                  30

Arg Leu Gln Pro Thr Trp Asn Asp Leu Gly Lys Tyr Asn Ser Met Glu
        35                  40                  45

Asp Ala Lys Val Tyr Val Ala Lys Val Asp Cys Thr Ala His Ser Asp
    50                  55                  60

Val Cys Ser Ala Gln Gly Val Arg Gly Tyr Pro Thr Leu Lys Leu Phe
65                  70                  75                  80

Lys Pro Gly Gln Glu Ala Val Lys Tyr Gln Gly Pro Arg Asp Phe Gln
                85                  90                  95

Thr Leu Glu Asn Trp Met Leu Gln Thr Leu Asn Glu
            100                 105

```
<210> SEQ ID NO 18
<211> LENGTH: 108
<212> TYPE: PRT
<213> ORGANISM: Homo sapiens
<220> FEATURE:
<223> OTHER INFORMATION: TXNDC5 Trx2

<400> SEQUENCE: 18
```

Gly Leu Tyr Glu Leu Ser Ala Asn Phe Glu Leu His Val Ala Gln Gly
1               5                   10                  15

-continued

```
Asp His Phe Ile Lys Phe Phe Ala Pro Trp Cys Gly His Cys Lys Ala
             20              25              30

Leu Ala Pro Thr Trp Glu Gln Leu Ala Leu Gly Leu Glu His Ser Glu
         35              40              45

Thr Val Lys Ile Gly Lys Val Asp Cys Thr Gln His Tyr Glu Leu Cys
         50              55              60

Ser Gly Asn Gln Val Arg Gly Tyr Pro Thr Leu Leu Trp Phe Arg Asp
65                   70              75                  80

Gly Lys Lys Val Asp Gln Tyr Lys Gly Lys Arg Asp Leu Glu Ser Leu
                 85              90              95

Arg Glu Tyr Val Glu Ser Gln Leu Gln Arg Thr Glu
             100             105
```